US009512195B2

(12) United States Patent
Madsen et al.

(10) Patent No.: US 9,512,195 B2
(45) Date of Patent: *Dec. 6, 2016

(54) INSULIN DERIVATIVES CONTAINING ADDITIONAL DISULFIDE BONDS

(71) Applicant: Novo Nordisk A/S, Bagsvaerd (DK)

(72) Inventors: Peter Madsen, Bagsvaerd (DK); Frantisek Hubalek, Herlev (DK); Thomas Boerglum Kjeldsen, Virum (DK); Svend Ludvigsen, Lynge (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/471,258

(22) Filed: Aug. 28, 2014

(65) Prior Publication Data

US 2014/0371140 A1  Dec. 18, 2014

Related U.S. Application Data

(63) Continuation of application No. 13/805,774, filed as application No. PCT/EP2011/060383 on Jun. 21, 2011, now Pat. No. 8,853,155.

(60) Provisional application No. 61/359,150, filed on Jun. 28, 2010, provisional application No. 61/359,500, filed on Jun. 29, 2010.

(30) Foreign Application Priority Data

Jun. 23, 2010 (EP) ..................................... 10167033
Jun. 23, 2010 (EP) ..................................... 10167046

(51) Int. Cl.
*A61K 38/00* (2006.01)
*A61K 38/38* (2006.01)
*C07K 14/62* (2006.01)

(52) U.S. Cl.
CPC ..................................... *C07K 14/62* (2013.01)

(58) Field of Classification Search
CPC .................................................... A61K 38/28
See application file for complete search history.

(56) References Cited

U.S. PATENT DOCUMENTS

| 8,815,798 B2 | 8/2014 | Ludvigsen et al. |
| 8,883,722 B2 | 11/2014 | Hubalek et al. |
| 2012/0184488 A1 | 7/2012 | Weiss |

FOREIGN PATENT DOCUMENTS

| CN | 101541830 A | 9/2009 |
| JP | S62-53999 A | 3/1987 |
| JP | H07309896 A | 11/1995 |
| JP | 2001-521004 A | 11/2001 |
| JP | 2007534613 A | 11/2007 |
| RU | 2207874 C2 | 7/2003 |
| WO | 92/00321 A1 | 1/1992 |
| WO | 2005/012347 A2 | 2/2005 |
| WO | 2007/081824 A2 | 7/2007 |
| WO | 2007/135117 A2 | 11/2007 |
| WO | 2008/034881 A1 | 3/2008 |
| WO | 2009022013 A1 | 2/2009 |
| WO | 2009087081 A2 | 7/2009 |
| WO | 2009/112583 A2 | 9/2009 |
| WO | 2010/066636 A1 | 6/2010 |

OTHER PUBLICATIONS

Brems et al., "Improved Insulin Stability Through Amino Acid . . . ", Protein Engineering, vol. 5(6), pp. 519-525 (1992).
Brange et al., "Insulin Structure and Stability," Pharm. Biotechnology, vol. 5, pp. 315-350 (1993).
Mansfeld et al., "Extreme Stabilization of a Thermolysin-Like . . . ", J. Biol. Chem, vol. 272(17), pp. 11152-11156 (1997).
Matsumura et al., "Stabilization of Phase T4 Iysozyme by Engineered . . . ", Proc. Natl Acad Sci USA, vol. 86, pp. 6562-6566 (1989).
Wetzel et al., "Disulfide Bonds and Thermal Stability in T4 Lysozyme . . . ", Proc Natl Acad Sci USA, vol. 85, pp. 401-405 (1988).
Almog et al., "Structural Basis of Thermostability," J. Biol. Chem., vol. 277(30), pp. 27553-27558 (2002).
Arnold et al., "Natural and Engineered Ribonucleases as . . . ", Biotechnol Letters, vol. 28, pp. 1615-1622 (2006).
Pace, C. N., "Conformational Stability of Globular Proteins," Trends Biochem Sci, vol. 15(1), pp. 14-17 (1990).
McAuley et al., "Contributions of Disulfide Bond to the Structure . . . ", Protein Science, vol. 17(1), pp. 95-106 (2008).
Hagihara et al., "Stabilization of an Immunoglobulin Fold Domain," J. Biol Chem, vol. 282(50), pp. 36489-36495 (2007).
Creighton, Thomas E., "Protein Folding Pathways Determined Using . . . ", Bioessays, vol. 14(3), pp. 195-199 (1992).
Clarke et al., "The Effects of Disulfide Bonds on the Denatured . . . ", Protein Sci., vol. 9, pp. 2394-2404 (2000).
Clarke et al., "Engineered Disulfide Bonds as Probes of the . . . ", Biochemistry, vol. 32(16), pp. 4322-4329 (1993).
Ikeguchi et al., "Contribution of the 6-120 Disulfide Bond of a . . . ", Biochemistry, vol. 31(50), pp. 12695-12700 (1992).
Dolginova et al., "Chemical Modification of Torpedo . . . ", Biochemistry, vol. 31, pp. 12248-12254 (1992).
Vogl et al., "Mechanism of Protein Stabilization by Disulfide," J. Mol. Biol., vol. 254(3), pp. 481-496 (1995).
Landenstein R. et al., "Protein Disulfides and Protein Disulfide . . . ", FEBS, vol. 273, pp. 4170-4185 (2006).
Mallick et al., "Genomic Evidence That the Intracellular Proteins . . . ", Proc. Natl Acad Sci USA, vol. 99(19), pp. 9679-9684 (2002).
Peer Bork, Power and Pitfalls in Sequence Analysis: The 70% Hurdle, Genome Research, 2000, 398-400, vol. 10.
Eliane Lazar et al., Transforming Growth Factor alpha : Mutation of Aspartic Acid 47 and Leucine 48 Results in different Biological Activities, Molecular and Cellular Biology, 1988, vol. 8,1247-1252.

(Continued)

*Primary Examiner* — Gyan Chandra
(74) *Attorney, Agent, or Firm* — Jianjie Hu

(57) ABSTRACT

The present invention is related to insulin derivatives containing additional disulfide bonds and methods of making such.

5 Claims, 4 Drawing Sheets

(56) References Cited

OTHER PUBLICATIONS

Wilson H. Burgess et al., Possible dissociation of the Heparin-binding and Mitogenic Activities of Heparin-binding (Acidic Fibroblast) Growth Factor-1 from its Receptor-binding Activities by Site-directed Mutagenesis of a Single Lysine Residue, The Journal of Cell Biology, 1990, 2129-2138, vol. 111.

James U. Bowie et al., Deciphering the message in protein sequences: Tolerance to Amino Acid Substitutions, Science, 1990, 1306-1310, vol. 247.

Chang, B.S. et al., Practical Approaches to Protein Formulation Development, Rational Design of Stable Protein Formulations-theory and practice (J.F. Carpenter and M. C. Manning eds.), 2002, 1-28.

Treetharnmathurot B. et al, Effect of PEG molecular weight and linking chemistry on the biological activity and thermal stability of PEGylated trypsin, International Journal of Pharmaceutics, 2008, v. 357, p. 252-259.

Moldogazieva N. T. et al., Structure-activity relationships in molecule of alfa-fetoprotein: conformational conditions and biological activity thereof, Biomedical chemistry, 2005, vol. 51, issue 2, pp. 127-151.

SEQUENCE LISTING

<160> NUMBER OF SEQ ID NOS: 2

<210> SEQ ID NO 1
<211> LENGTH: 21
<212> TYPE: PRT

```
<213> ORGANISM: Artificial
<220> FEATURE:
<223> OTHER INFORMATION: Modified Insulin A chain
<220> FEATURE:
<221> NAME/KEY: DISULFID
<222> LOCATION: (6)..(6)
<220> FEATURE:
<221> NAME/KEY: DISULFID
<222> LOCATION: (7)..(7)
<220> FEATURE:
<221> NAME/KEY: DISULFID
<222> LOCATION: (10)..(10)
<220> FEATURE:
<221> NAME/KEY: DISULFID
<222> LOCATION: (11)..(11)
<220> FEATURE:
<221> NAME/KEY: DISULFID
<222> LOCATION: (20)..(20)

<400> SEQUENCE: 1

Gly Ile Val Glu Gln Cys Cys Thr Ser Cys Cys Ser Leu Glu Gln Leu
1               5                   10                  15

Glu Asn Tyr Cys Asn
            20

<210> SEQ ID NO 2
<211> LENGTH: 29
<212> TYPE: PRT
<213> ORGANISM: Artificial
<220> FEATURE:
<223> OTHER INFORMATION: Modified Insulin B chain
<220> FEATURE:
<221> NAME/KEY: DISULFID
<222> LOCATION: (4)..(4)
<220> FEATURE:
<221> NAME/KEY: DISULFID
<222> LOCATION: (7)..(7)
<220> FEATURE:
<221> NAME/KEY: DISULFID
<222> LOCATION: (19)..(19)
<220> FEATURE:
<221> NAME/KEY: MOD_RES
<222> LOCATION: (29)..(29)
<223> OTHER INFORMATION: Xaa is Lys-(N(epsilon)-Octadecanedioyl-gGlu-
    OEG-OEG)

<400> SEQUENCE: 2

Phe Val Asn Cys His Leu Cys Gly Ser His Leu Val Glu Ala Leu Tyr
1               5                   10                  15

Leu Val Cys Gly Glu Arg Gly Phe His Tyr Thr Pro Xaa
            20                  25
```

INSULIN DERIVATIVES CONTAINING ADDITIONAL DISULFIDE BONDS

CROSS REFERENCE TO RELATED APPLICATIONS

This application is a continuation of U.S. application Ser. No. 13/805,774, filed Mar. 7, 2013, which is a 35 U.S.C. §371 National Stage application of International Application PCT/EP2011/060383, filed Jun. 21, 2011, which claimed priority of European Patent Application 10167033.9, filed Jun. 23, 2010 and European Patent Application 10167046.1, filed Jun. 23, 2010; this application claims priority under 35 U.S.C. §119 of U.S. Provisional Application 61/359,150, filed Jun. 28, 2010 and U.S. Provisional Application 61/359,500, filed Jun. 29, 2010; the contents of which are incorporated herein.

FIELD OF THE INVENTION

The present invention is related to insulin derivatives containing additional disulfide bonds and methods of making such.

BACKGROUND OF THE INVENTION

Diabetes mellitus is a metabolic disorder in which the ability to utilize glucose is partly or completely lost. In the treatment of diabetes mellitus, many varieties of insulin formulations have been suggested and used, such as regular insulin, isophane insulin (designated NPH), insulin zinc suspensions (such as Semilente®, Lente®, and Ultralente®), and biphasic isophane insulin.

Human insulin consists of two polypeptide chains, the A and B chains which contain 21 and 30 amino acid residues, respectively. The A and B chains are interconnected by two disulfide bridges. Insulin from most other species is similar, but may contain amino acid substitutions in some positions. Within the last decade a number of human insulin analogues have been developed. They are designed for particular profiles of action, i.e. fast acting or prolonged action. Commercially available products comprising such insulin analogues include Levemir®, NovoRapid®, Humalog®, Apidra® and Lantus®.

Human insulin is rapidly degraded in the lumen of gastrointestinal tract by the action of multiple proteases limiting its absorption into circulation. Insulin analogues that are hydrophilic and stabilized towards proteolytic degradation show higher bioavailability in animal models when compared to native insulin.

Incorporation of disulfide bonds into proteins is one of nature's ways of improving protein stability; a correlation between the abundance of disulfide bonds and the maximum growth temperature among thermophilic organisms has been found, implicating the importance of disulfide bonds in protein stabilization in high temperature environments (Mallick P, et al, 2002, Proc. Natl. Acad. Sci. USA, 99, 9679-9684.; Ladenstein R, et al, 2006, FEBS J., 273, 4170-4185). There are also many examples of disulfide bonds being successfully engineered into proteins with concomitant increases in stability. One of the largest stabilizations was achieved for RNAse barnase (Clarke J., Fersht A., 1993, Biochem., 32, 4322-4329). Such stabilization is brought about by increasing the activation energy required for unfolding or by constraining the unfolded conformations of the protein and thereby decreasing their conformational entropy (Pace C. N., 1990, Trends Biol. Sci., 14-17). However, much more needs to be learned in this emerging area of research. To date, there are no reports of engineered disulfide bonds in insulin.

There is still a need for novel insulin derivatives which are stable.

SUMMARY OF THE INVENTION

The present invention is related to insulin derivatives having two or more cysteine substitutions and a side-chain attached to the insulin, where the three disulfide bonds of human insulin are retained, and the sites of cysteine substitutions are chosen in such a way that the introduced cysteine residues are placed in the three dimensional structure of the folded insulin derivative to allow for the formation of one or more additional disulfide bonds not present in human insulin.

In one aspect an insulin derivative of the invention is obtained, wherein the sites of cysteine substitutions are chosen in such a way that (1) the introduced cysteine residues are placed in the three dimensional structure of the folded insulin derivative to allow for the formation of one or more additional disulfide bonds not present in human insulin, and (2) the insulin derivative retains the desired biological activities associated with human insulin.

In one aspect an insulin derivative of the invention is obtained, wherein the sites of cysteine substitutions are chosen in such a way that (1) the introduced cysteine residues are placed in the three dimensional structure of the folded insulin derivative to allow for the formation of one or more additional disulfide bonds not present in human insulin, (2) the insulin derivative retains the desired biological activities associated with human insulin, and (3) the insulin derivative has increased physical stability relative to human insulin and/or insulin derivative without one or more additional disulfide bonds.

In one aspect an insulin derivative of the invention is obtained, wherein the sites of cysteine substitutions are chosen in such a way that (1) the introduced cysteine residues are placed in the three dimensional structure of the folded insulin derivative to allow for the formation of one or more additional disulfide bonds not present in human insulin, (2) the insulin derivative retains the desired biological activities associated with human insulin, and (3) the insulin derivative is stabilized against proteolytic degradation.

Herein is also described a method for stabilizing an insulin derivative comprising substituting two or more amino acids of an insulin with cysteine residues and attaching a side-chain to the insulin, wherein a. the three disulfide bonds of human insulin are retained and b. the sites of cysteine substitutions are chosen in such a way that the introduced cysteine residues are placed in the three dimensional structure of the folded insulin derivative to allow for the formation of one or more additional disulfide bonds not present in human insulin, thereby creating an insulin derivative comprising one or more additional disulfide bonds not present in human insulin.

DESCRIPTION OF THE INVENTION

Figure 1:
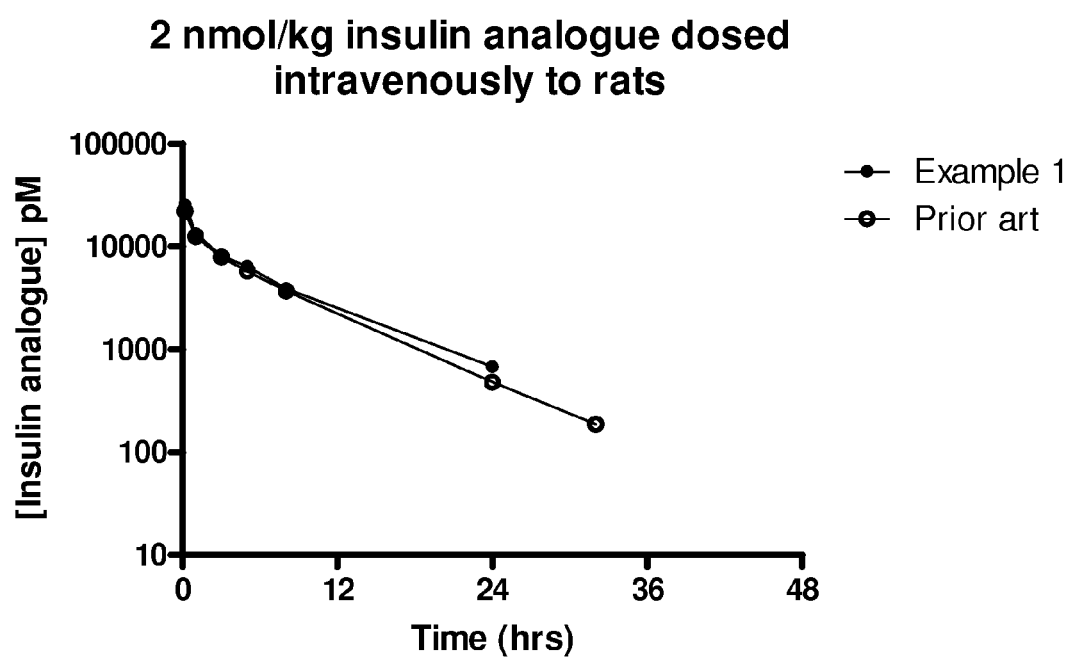
FIG. 1: Comparison of i.v. PK profiles in rats of the derivative of example 1 compared to the similar derivative without an additional disulfide bond.
Figure 2:
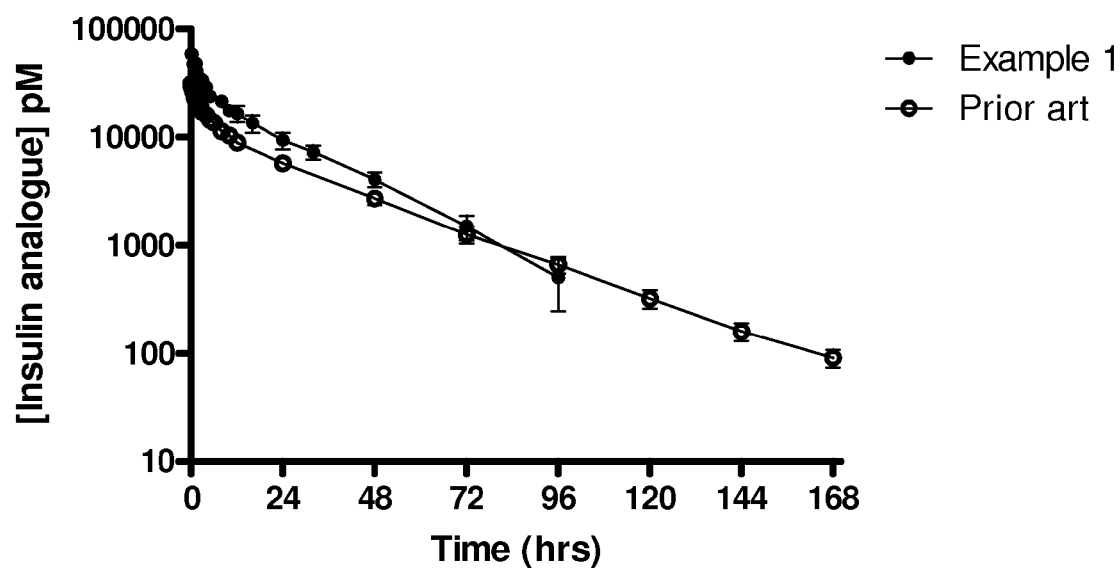
FIG. 2: Comparison of i.v. PK profiles in dogs of the derivative of example 1 compared to the similar derivative without an additional disulfide bond.

In the present invention novel insulin derivatives are presented wherein disulfide bonds are engineered into the insulin derivatives.

In one aspect an insulin derivative according to the invention has two or more cysteine substitutions and the three disulfide bonds of human insulin are retained.

In one aspect an insulin derivative of the invention has a side-chain. In one aspect the side-chain is attached to the epsilon amino group of a lysine residue. In one aspect the side-chain is attached to the epsilon amino group of a lysine residue in the B-chain.

In one aspect an insulin derivative according to the invention has two or more cysteine substitutions, the three disulfide bonds of human insulin retained and a side-chain which is attached to the epsilon amino group of a lysine residue such as in the B-chain.

In one aspect of the invention, the sites of cysteine substitutions are chosen in such a way that the introduced cysteine residues are placed in the three dimensional structure of the folded insulin derivative to allow for the formation of one or more additional disulfide bonds not present in human insulin.

It has by the inventors been found that the insulin derivatives according to the invention have improved physical stability. It has thus been found that the tendency of the insulin derivatives according to the invention to form biologically inactive and/or insoluble aggregates of the insulin analogues is reduced for example as a result of exposure of the analogues to thermo-mechanical stresses and/or interaction with interfaces and surfaces that are destabilizing, such as hydrophobic surfaces and interfaces.

The human insulin derivatives according to the invention bind to the insulin receptor. It has thus surprisingly been found by the inventors that the human insulin derivatives according to the invention have both improved physical stability and retain binding to the insulin receptor.

In one aspect, insulin derivatives according to the invention, i.e. containing one or more additional disulfide bonds, are more protracted than similar insulin derivatives without one or more additional disulfide bonds. With "more protracted" is herein meant that they have a longer elimination half-life or in other words an insulin effect for an extended period, i.e. a longer duration of action. It has thus surprisingly been found by the inventors that insulin derivatives comprising one or more disulfide bonds may have a long elimination half-life or in other words an insulin effect for an extended period, or a protracted duration of action compared to the similar insulin derivatives without one or more additional disulfide bonds.

In one aspect the insulin derivatives of the invention are stabilized against proteolytic degradation, i.e. against rapid degradation in the gastro intestinal (GI) tract or elsewhere in the body. In one aspect the insulin derivatives of the invention are stabilized against proteolytic degradation relative the insulin derivative without one or more additional disulfide bonds.

An insulin derivative which is stabilized against proteolytic degradation is herein to be understood as an insulin derivative, which is subjected to slower degradation by one or more proteases relative to human insulin. In one embodiment an insulin derivative according to the invention is subjected to slower degradation by one or more proteases relative to human insulin. In a further embodiment of the invention an insulin derivative according to the invention is stabilized against degradation by one or more enzymes selected from the group consisting of: pepsin (such as e.g. the isoforms pepsin A, pepsin B, pepsin C and/or pepsin F), chymotrypsin (such as e.g. the isoforms chymotrypsin A, chymotrypsin B and/or chymotrypsin C), trypsin, Insulin-Degrading Enzyme (IDE), elastase (such as e.g. the isoforms pancreatic elastase I and/or II), carboxypeptidase (e.g. the isoforms carboxypeptidase A, carboxypeptidase A2 and/or carboxypeptidase B), aminopeptidase, cathepsin D and other enzymes present in intestinal extracts derived from rat, pig or human.

In one embodiment an insulin derivative according to the invention is stabilized against degradation by one or more enzymes selected from the group consisting of: chymotrypsin, trypsin, Insulin-Degrading Enzyme (IDE), elastase, carboxypeptidases, aminopeptidases and cathepsin D. In a further embodiment an insulin derivative according to the invention is stabilized against degradation by one or more enzymes selected from the group consisting of: chymotrypsin, carboxypeptidases and IDE. In a yet further embodiment an insulin derivative according to the invention is stabilized against degradation by one or more enzymes selected from: chymotrypsin and IDE. In a yet further embodiment an insulin derivative according to the invention is stabilized against degradation by one or more enzymes selected from: chymotrypsin and carboxypeptidases.

A "protease" or a "protease enzyme" is a digestive enzyme which degrades proteins and peptides and which is found in various tissues of the human body such as e.g. the stomach (pepsin), the intestinal lumen (chymotrypsin, trypsin, elastase, carboxypeptidases, etc.) or mucosal surfaces of the GI tract (aminopeptidases, carboxypeptidases, enteropeptidases, dipeptidyl peptidases, endopeptidases, etc.), the liver (Insulin degrading enzyme, cathepsin D etc), and in other tissues.

T½ may be determined as described in example 102 as a measure of the proteolytical stability of an insulin derivative according to the invention towards protease enzymes such as chymotrypsin, pepsin and/or carboxypeptidase A or towards a mixture of enzymes such as tissue extracts (fromliver, kidney, duodenum, jejunum, ileum, colon, stomach, etc.). In one embodiment of the invention T½ is increased relative to human insulin. In a further embodiment T½ is increased relative to the insulin derivative without one or more additional disulfide bonds. In a yet further embodiment T½ is increased at least 2-fold relative to human insulin. In a yet further embodiment T½ is increased at least 2-fold relative to the insulin derivative without one or more additional disulfide bonds. In a yet further embodiment T½ is increased at least 3-fold relative to human insulin. In a yet further embodiment T½ is increased at least 3-fold relative to the insulin derivative without one or more additional disulfide bonds. In a yet further embodiment T½ is increased at least 4-fold relative to human insulin. In a yet further embodiment T½ is increased at least 4-fold relative to the insulin derivative without one or more additional disulfide bonds. In a yet further embodiment T½ is increased at least 5-fold relative to human insulin. In a yet further embodiment T½ is increased at least 5-fold relative to the insulin derivative without one or more additional disulfide bonds. In a yet further embodiment T½ is increased at least 10-fold relative to human insulin. In a yet further embodiment T½ is increased at least 10-fold relative to the insulin derivative without one or more additional disulfide bonds.

In one aspect, an insulin derivative according to the invention has improved chemical stability. In one aspect, an insulin derivative according to the invention has improved physical stability. In one aspect, an insulin derivative according to the invention has improved chemical and physical stability.

In one aspect, an insulin derivative according to the invention has improved chemical and/or physical stability relative to human insulin. In one aspect, an insulin derivative according to the invention has improved chemical and/or physical stability relative to the insulin derivative without one or more additional disulfide bonds.

The term "physical stability" as used herein refers to the tendency of the insulin derivaitive to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical instability thus involves conformational changes relative to human insulin, which includes loss of higher order structure, aggregation, fibrillation, precipitation and/or adsorption to surfaces. Peptides such as insulin are known to be prone to instability due to e.g. fibrillation. Physical stability of a solution comprising the insulin derivative may be evaluated by conventional means of e.g. visual inspection, nephelometry and/or turbidity measurements after exposing the solutionfilled in suitable containers (e.g. cartridges or vials) to mechanical/physical stress (e.g. agitation) at different temperatures for various time periods. Visual inspection of the solution is performed in a sharp focused light with a dark background. The turbidity of the solution is characterized by a visual score ranking the degree of turbidity for instance on a scale from 0 to 3 (a solution showing no turbidity corresponds to a visual score 0, and a solution showing visual turbidity in daylight corresponds to visual score 3). A solution is classified physical unstable with respect to protein aggregation, when it shows visual turbidity in daylight. Alternatively, the turbidity of the solution can be evaluated by simple turbidity measurements well-known to the skilled person. Physical stability of the insulin derivative can also be evaluated by using a spectroscopic agent or probe of the conformational status of the insulin derivative. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths. Physical stability of the insulin derivatives of the invention may e.g. be determined as described in example 109.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the insulin derivative as used herein refers to chemical covalent changes in the protein structure leading to formation of chemical degradation products with potential less biological potency and/or potential increased immunogenic properties compared to the native protein structure and involves avoidance of degradation of covalent bonds, such as hydrolysis, racemization, oxidation or crosslinking. Various chemical degradation products can be formed depending on the type and nature of the native protein and the environment to which the insulin derivative is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutamine or asparagine residues is hydrolysed to form a free carboxylic acid. Asparagine and aspartic acid residues may further form isoAsp degradation products. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., *Plenum Press*, New York 1992). Oxidation (of for instance methionine residues) and racemization can be mentioned as another variant of chemical degradation. The chemical stability of the insulin derivative can be evaluated by measuring the amount of the chemical degradation products at various time-points after exposure to different environmental conditions (the formation of degradation products can often be accelerated by for instance increasing temperature). The individual degradation products are often determined by separation of the degradation products depending on molecule size and/or charge e.g. using a combination of chromatographic (e.g. SEC-HPLC, RP-HPLC or IE-HPLC) and spectroscopic methods (various mass spectrometry methods) sometimes in combinations with chemical/enzymatic fragmentation.

In one embodiment, the insulin derivative of the invention has improved chemical stability relative to that of the insulin derivative without one or more additional disulfide bonds when tested as described in the examples.

In one embodiment, the insulin derivative of the invention has increased hydrophilicity relative to that of human insulin and/or the insulin derivative without one or more additional disulfide bonds when tested for hydrophobicity as known by the skilled person and e.g. described in example 101.

In one embodiment, the insulin derivative of the invention has little or no tendency to aggregate. The aggregation tendency is preferably significantly improved relatively to the aggregation tendency of human insulin and/or the insulin derivative without one or more additional disulfide bonds when tested in a thioflavin assay.

In one aspect, an insulin derivative according to the invention has improved thermodynamic stability such as e.g. folding stability, conformational stability and/or higher melting temperature.

When used herein an insulin derivative is said to have improved "thermodynamic stability" if denaturation of said derivative requires higher stress level such as higher temperature and/or higher concentration of denaturation agent in comparison to human insulin or an insulin derivative without one or more additional disulfide bonds.

Conformational stability may be evaluated by circular dichroism and NMR as e.g. described by Hudson and Andersen, Peptide Science, vol 76 (4), pp. 298-308 (2004). Melting temperature is understood as the temperature at which an insulin structure is reversibly or irreversibly changed. Higher melting temperature corresponds to more stable structures. Melting temperature can be determined e.g. by evaluating conformational stability by circular dichroism and/or NMR as a function of temperature or by differential scanning calorimetry. Thermodynamic stability can also be determined by CD spectroscopy and or NMR in the presence of increasing concentration of denaturation agent, such as for example guanidinium hydrochloride. Free energy of unfolding as described previously (Kaarsholm, N. C., et al, 1993, *Biochemistry*, 32, 10773-8) can be determined from such experiments. Upon protein denaturation, negative CD in the far UV range (240-218-nm) gradually diminishes, consistent with the loss of ordered secondary structure that accompanies protein unfolding (Holladay et al., 1977, *Biochim. Biophys.Acta*, 494, 245-254; Melberg and Johnson, 1990, *Biochim. Biophys.Acta*, 494, 245-254). The insulin CD spectrum in the near UV range (330-250-nm) reflects the environment of the tyrosine chromophore with contributions from the disulfide bonds (Morris et al., 1968, *Biochim.Biophys. Acta.*, 160, 145-155; Wood et al., 1975, *Biochim. Biophys. Acta*, 160, 145-155; Strickland & Mercola, 1976, *Biochemistry*, 15, 3875-3884). The free energy of unfolding of insulin was previously calculated from such studies to be 4.5 kcal/mol (Kaarsholm, N. C., et al, 1993, *Biochemistry*, 32, 10773-8).

Insulin CD spectrum in the near UV range (330-250-nm) reflects the environment of the tyrosine chromophore with contributions from the disulfide bonds. Since tyrosine residues are part of the insulin's dimer surface, changes in molar elipticity at this region (especially at 276 nm) reflect on insulin's association state. Another way to measure insulin's association state is by application of size-exclusion chromatography under non-dissociating conditions as known in the art and described in the examples.

An insulin derivative according to the invention may have substantially the same or increased in vivo potency relative to the parent insulin. In one aspect an insulin derivative of the invention has substantially the same in vivo potency relative to the parent insulin. In one aspect an insulin derivative of the invention has increased in vivo potency relative to the parent insulin.

Standard assays for measuring insulin in vivo potency are known to the person skilled in the art and include assays described in the examples, such as; Potency of insulin derivatives of the invention relative to human insulin, intravenous steady-state clamp assays such as rat pharmacokinetics and rat PK following intraintestinal injection, blood glucose lowering effect and intravenous rat PK assays.

An insulin derivative according to the invention may have substantially the same or increased in vitro potency relative to the parent insulin. In one aspect an insulin derivative of the invention has substantially the same in vitro potency relative to the parent insulin. In one aspect an insulin derivative of the invention has increased in vitro potency relative to the parent insulin.

Standard assays for measuring insulin in vitro potency are known to the person skilled in the art and include inter alia the below in vitro assays:

(1) insulin radioreceptorassays, in which the relative potency of an insulin is defined as the ratio of insulin to insulin derivative required to displace 50% of $^{125}$I-insulin specifically bound to insulin receptors present on cell membranes, e.g. a rat liver plasma membrane fraction;
(2) lipogenesis assays, performed e.g. with rat adipocytes, in which relative insulin potency is defined as the ratio of insulin to insulin derivative required to achieve 50% of the maximum conversion of [3-$^3$H] glucose into organic-extractable material (i.e. lipids); and
(3) glucose oxidation assays in isolated fat cells in which the relative potency of the insulin derivative is defined as the ratio of insulin to insulin derivative to achieve 50% of the maximum conversion of glucose-1-[$^{14}$C] into [$^{14}$CO$_2$].

Disulfide bonds are derived by the coupling of two thiol groups and are herein to be understood as the linkage between two sulfur atoms, i.e. a structure having the overall connectivity R—S—S—R. Disulfide bonds may also be called connecting disulfide bonds, SS-bonds or disulfide bridges. A disulfide bond is created by the introduction of two cysteine amino acid residues to a peptide with subsequent oxidation of the two thiol groups to a disulfide bond. Such oxidation can be performed chemically (as known by persons skilled in the art) or can happen during insulin expression in e.g. yeast.

When introducing cysteine residues into the insulin derivative without one or more additional disulfide bonds, the cysteine residues are placed in the three dimensional structure of the folded insulin analogue to allow for the formation of one or more additional disulfide bonds not present in human insulin. For example, if placing two new cysteine residues, the proximity of the new cysteine residues in the three dimensional structure is such that a disulfide bond can be formed between the two new cysteine residues.

The number of disulfide bonds in a protein (such as insulin) can be readily determined by accurate intact mass measurements as described, for example in the Examples. The disulfide bonds connectivity can be verified (determined) by standard techniques known in the art, such as peptide mapping. The general strategy for disulfide bond mapping in an insulin peptide includes the following steps: 1) Fragmentation of the non-reduced insulin into disulfide bonded peptides containing, if possible, only a single disulfide bond per peptide. The chosen conditions is also such that rearrangement of disulfide bonds is avoided, 2) Separation of disulfide bonded peptides from each other. 3) Identification of the cysteine residues involved in the individual disulfide bonds.

Human insulin is typically digested by Glu-C protease yielding peptide I containing two disulfide bonds (A6-A11 and A7-B7) and peptide II containing a single disulfide bond (A20-B19). To unambiguously assign the disulfide bonds in peptide I, further fragmentation is necessary. Acid hydrolysis (Ryle at al., 1955 Biochem J. 60, 541-56), manual Edman degradation (Kumazaki T, Ishii, S. 1990 J. Biochem (Tokyo) 17, 414-9). or prolonged digestion with thermolysin (Ota M, Ariyoshi, Y., 1995, Biosci. Biotech. Biochem. 59, 1956-7) were previously employed to hydrolyze CysCys bonds in proteins. An alternative way to assign the disulfide bonds in peptide I is a partial reduction with triscarboxyethyl phosphine (reduction of A7-B7 disulfide bond), alkylation of the reduced cysteine residues followed by complete reduction and cysteine alkylation using a different alkyl group (Yen, T.-Y., Yan, H., Macher, B., 2001 J Mass Spectrom. 37, 15-30). The strategy for disulfide mapping of insulins containing extra disulfide bonds is in principle the same as outline above for human insulin adjusted for each analogue in such a way that accommodates the new disulfide bond. Determination of insulin structure by NMR or X-ray crystallography is an alternative approach for verifying the disulfide bond connectivity. Conditions for solving NMR and/or X-ray structures of insulin have been described previously and are known in the art.

In one aspect of the invention an insulin derivative which has a side chain and at least two cysteine substitutions is provided, where the three disulfide bonds of human insulin are retained.

With the term "cysteine substitution" is herein meant replacing an amino acid which is present in human insulin with a cysteine. For example, isoleucine in position 10 in the A chain (IleA10) and glutamine in position 4 of the B chain of human insulin (GlnB4) may each be replaced by a cysteine residue. With the term "other amino acid residue substitution" is herein meant replacing an amino acid which is present in human insulin with an amino acid which is not cysteine.

The term "human insulin" as used herein means the human insulin hormone whose two dimensional and three dimensional structures and properties are well-known. The three dimensional structure of human insulin has been e.g. determined by NMR and X-ray crystallography under many different conditions and many of these structures are deposited in the Protein data bank (http://www.rcsb.org). Non-limiting examples of a human insulin structure is the T6 structure (http://www.rcsb.org/pdb/explore.do?structureId=1MSO) and the R6 structure (http://www.rcsb.org/pdb/explore.do?structureId=1EV3). Human insulin has two polypeptide chains, named the A-chain and the B-chain. The A-chain is a 21 amino acid peptide and the B-chain is a 30 amino acid peptide, the two chains being connected by disulfide bonds: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain. Thus "an insulin derivative where the three disulfide bonds of human insulin are retained" is herein understood as an insulin derivative comprising the three disulfide bonds of human insulin, i.e. a disulfide bond between the cysteine in position 7 of the A-chain and the cysteine in position 7 of the B-chain, a disulfide bond between the cysteine in position 20 of the A-chain and the cysteine in position 19 of the B-chain and a disulfide bond between the cysteines in position 6 and 11 of the A-chain.

In the human body, the insulin hormone is synthesized as a single-chain precursor proinsulin (preproinsulin) consisting of a prepeptide of 24 amino acids followed by proinsulin containing 86 amino acids in the configuration: prepeptide-B-Arg Arg-CLys Arg-A, in which C is a connecting peptide of 31 amino acids. Arg-Arg and Lys-Arg are cleavage sites for cleavage of the connecting peptide from the A and B chains.

In one aspect of the invention an insulin derivative which has two or more cysteine substitutions is provided, where the three disulfide bonds of human insulin are retained, and wherein at least one amino acid residue in a position selected from the group consisting of A9, A10 and A12 of the A-chain is substituted with a cysteine, at least one amino acid residue in a position selected from the group consisting of B1, B2, B3, B4, B5 and B6 of the B-chain is substituted with a cysteine, a side chain is attached to the epsilon amino group of a lysine residue in the B-chain and optionally the amino acid in position B30 is deleted. In one aspect of the invention the amino acid residue in position A10 of the A-chain is substituted with a cysteine, at least one amino acid residue in a position selected from the group consisting of B1, B2, B3, and B4 of the B-chain is substituted with a cysteine, a side chain is attached to the epsilon amino group of a lysine residue in the B-chain and optionally the amino acid in position B30 is deleted. In one aspect of the invention at least one amino acid residue in a position selected from the group consisting of A9, A10 and A12 of the A-chain is substituted with a cysteine, at least one amino acid residue in a position selected from the group consisting of B1, B2, B3, B4, B5 and B6 of the B-chain is substituted with a cysteine, at least one amino acid residue in a position selected from the group consisting of A14, A21, B1, B3, B10, B16, B22, B25, B26, B27, B28, B29, B30, B31, B32 is substituted with an amino acid which is not a cysteine, a side chain is attached to the epsilon amino group of a lysine residue in the B-chain and optionally the amino acid in position B30 is deleted. It is understood that when B1 or B3 is cysteine, the same amino acid can not be an amino acid which is not cysteine, whereas if e.g. B1 is cysteine B3 may according to the aspect of the invention be substituted with an amino acid which is not a cysteine and vice versa. In one aspect of the invention, the amino acid residue in position A10 of the A-chain is substituted with a cysteine, at least one amino acid residue in a position selected from the group consisting of B1, B2, B3, and B4 of the B-chain is substituted with a cysteine, optionally at least one amino acid residue is substituted with an amino acid which is not a cysteine, a side chain is attached to the epsilon amino group of a lysine residue in the B-chain and optionally the amino acid in position B30 is deleted. In one aspect of the invention, the amino acid residue in position A10 of the A-chain is substituted with a cysteine, at least one amino acid residue in a position selected from the group consisting of B3 and B4 of the B-chain is substituted with a cysteine, optionally at least one amino acid residue is substituted with an amino acid which is not a cysteine, a side chain is attached to the epsilon amino group of a lysine residue in the B-chain and optionally the amino acid in position B30 is deleted. In one aspect of the invention, the amino acid residue in position A10 of the A-chain is substituted with a cysteine, the amino acid residue in position B3 of the B-chain is substituted with a cysteine, optionally at least one amino acid residue is substituted with an amino acid which is not a cysteine, a side chain is attached to the epsilon amino group of a lysine residue in the B-chain and optionally the amino acid in position B30 is deleted. In one aspect of the invention, the amino acid residue in position A10 of the A-chain is substituted with a cysteine, the amino acid residue in B4 of the B-chain is substituted with a cysteine, optionally at least one amino acid residue is substituted with an amino acid which is not a cysteine, a side chain is attached to the epsilon amino group of a lysine residue in the B-chain and optionally the amino acid in position B30 is deleted.

In one aspect, insulin derivatives according to the invention are obtained, wherein position B30 is deleted.

An additional disulfide bond obtained by the invention may be connecting two cysteines of the same chain, i.e. two cysteines in the A-chain or two cysteines in the B-chain of the insulin, or connecting a cysteine in the A-chain with a cysteine in the B-chain of the insulin. In one aspect, an insulin derivative according to the invention is obtained, wherein at least one additional disulfide bond is connecting two cysteines in the A-chain or connecting two cysteines in the B-chain. In one aspect, an insulin derivative according to the invention is obtained, wherein at least one additional disulfide bond is connecting a cysteine in the A-chain with a cysteine in the B-chain.

When used herein the term "additional disulfide bonds" means one or more disulfide bonds which are not present in human insulin.

In one aspect of the invention, cysteines are substituted into two positions of the insulin derivative, where the positions are selected from the group consisting of:
A10C, B1C;
A10C, B2C;
A10C, B3C;
A10C, B4C;
A10C, B5C; and
B1C, B4C.

In one aspect of the invention, cysteines are substituted into two positions of the insulin analogue, where the positions are selected from the group consisting of:
A10C, B1C;
A10C, B2C;
A10C, B3C;
A10C, B4C; and
B1C, B4C.

In one aspect of the invention, cysteines are substituted into two positions of the insulin derivative, where the positions are selected from the group consisting of:
A10C, B1C;
A10C, B2C;
A10C, B3C; and
A10C, B4C.

In one aspect of the invention, cysteines are substituted into two positions of the insulin analogue, where the positions are selected from the group consisting of:
A10C, B3C; and
A10C, B4C.

In one aspect of the invention, cysteines are substituted into two positions of the insulin analogue, where the positions are A10C and B3C.

In one aspect of the invention, cysteines are substituted into two positions of the insulin analogue, where the positions are A10C and B4C.

In one aspect of the invention, insulin derivatives of the invention comprise in addition to the cysteine substitutions one or more amino acids selected from the group consisting of: A8H, A14E, A14H, A18L, A21G, B1G, B3Q, B3E, B3T, B3V, B3K, B3L, B16H, B16E, B22E, B24G, B25A, B25H, B25N, B27E, B27D, B27P, B28D, B28E, B28K, desB1, desB24, desB25, desB27 and desB30. In one aspect of the invention, insulin derivatives of the invention comprise in addition to the cysteine substitutions one or more amino acids selected from the group consisting of: A8H, A14E, A21G, desB1, B1G, B3Q, B3E, B10E, B16H, B16E, B24G, B25H, B25A, B25N, B25G, desB27, B27E, B28E, B28D, and desB30.

In one aspect of the invention, insulin derivatives of the invention comprise in addition to the cysteine substitutions one or more amino acids selected from the group consisting of: A21G, desB1, B1G, B3Q, B3S, B3T and B3E.

In one aspect of the invention, insulin derivatives of the invention comprise in addition to the cysteine substitutions one or more amino acids selected from the group consisting of: A8H, A14E, A14H, B16H, B10E, B16E, B25H, B25A, B25N, B27E, B27P, desB27 and B28E.

In one aspect of the invention, insulin derivatives of the invention comprise in addition to the cysteine substitutions one or more amino acids selected from the group consisting of: B28E, B28D, desB27, and A14E.

In one aspect of the invention, insulin derivatives of the invention comprise in addition to the cysteine substitutions one or more amino acids selected from the group consisting of: B3K, B29E, B27E, B27D, desB27, B28E, B28D, B28K and B29P In one aspect of the invention, insulin derivatives of the invention comprise in addition to the cysteine substitutions a C-peptide connecting the C-terminus of the B-chain with the N-terminus of the A-chain (to form a so called single-chain insulin derivaitve). In one embodiment of the invention, the parent insulin is selected from the group consisting of single chain insulin analogues. In one embodiment of the invention, the parent insulin is selected from the group consisting of single chain insulin analogues listed in WO2007096332, WO2005054291 or WO2008043033, which patents are herein specifically incorporated by reference.

In one aspect of the invention, an insulin derivative is obtained which comprises two cysteine substitutions resulting in one additional disulfide bond relative to human insulin.

"An insulin" according to the invention is herein to be understood as human insulin, desB30 human insulin or an insulin analogue.

The term "insulin peptide" as used herein means a peptide which is either human insulin, desB30 human insulin or an analogue or a derivative thereof with insulin activity.

The term "insulin analogue" as used herein means a modified insulin wherein one or more amino acid residues of the insulin have been substituted by other amino acid residues and/or wherein one or more amino acid residues have been deleted from the insulin and/or wherein one or more amino acid residues have been added and/or inserted to the insulin.

In one aspect an insulin derivative according to the invention is an insulin analogue (as defined above) containing one or more additional disulfide bond(s) relative to human insulin and containing a side chain attached to the epsilon amino group of a lysine residue present in the B-chain of the molecule.

The term "insulin derivative" is intended to mean an insulin (as defined above) that has been chemically derivatised. This means that a side chain (as defined herein) has been coupled to the insulin. In the broadest sense, the side chain can be of any sort, such as PEG, but, more preferred, the side chain is containing a fatty acid or a fatty diacid moiety.

The term "parent insulin" as used herein is intended to mean an insulin with one or more additional disulfide bonds, i.e. human insulin, desB30 human insulin or an insulin analogue with one or more additional disulfide bonds, before being derivatized with a side chain.

The term "insulin derivative without one or more additional disulfide bonds" as used herein is intended to mean an insulin derivative having the three disulfide bonds naturally present in human insulin, i.e. a first bridge between the cysteine in position 7 of the A-chain and the cysteine in position 7 of the B-chain, a second bridge between the cysteine in position 20 of the A-chain and the cysteine in position 19 of the B-chain and a third bridge between the cysteines in position 6 and 11 of the A-chain, and a side chain attached to the insulin but no further disulfide bonds/bridges.

The term "side chain" is used hereinand is intended to mean a fatty acid or diacid (optionally via one or more linkers) coupled to the parent insulin of the invention, such as to the epsilon amino group of a lysine present in the B-chain of the parent insulin. The fatty acid or diacid part of the side chain is conferring affinity to serum albumin, and the linkers act either to modify (e.g. increase) the affinity for albumin, modify solubility of the insulin derivative, and/or modulate (increase/decrease) the affinity of the insulin derivative for the insulin receptor.

In one aspect an insulin derivative according to the invention is an insulin analogue comprising at least two cysteine substitutions, wherein the insulin analogue is acylated in one or more amino acids of the insulin peptide.

Herein, the term "acylated insulin" covers modification of human insulin or an insulin analogue by attachment of one or more acyl moieties via a linker to the insulin.

A non-limiting example of insulin derivatives in the form of acylated insulin analogues which may be modified by cysteine substitutions according to the invention may e.g. be found in WO 2009/115469 A1.

In one embodiment an insulin derivative according to the invention is a modified insulin wherein two amino acid residues have been substituted by cysteine residues, a side chain has been introduced and optionally the amino acid in position B30 has been deleted relative to the amino acid sequence of human insulin.

larly, terms like B1, B2 and B3 etc. indicates the amino acid in position 1, 2 and 3 etc., respectively, in the B chain of insulin (counted from the N-terminal end). Using the one letter codes for amino acids, a term like A10C designates that the amino acid in the A10 position is cysteine. Using the three letter codes for amino acids, the corresponding expression is A10Cys.

By "desB30", "B(1-29)" or "des-ThrB30" is meant a natural insulin B chain or an analogue thereof lacking the B30 (threonine, Thr) amino acid and "A(1-21)" means the natural insulin A chain. Thus, e.g., A10C,B1C,desB30 human insulin or alternatively A10Cys,B1Cys,desB30 human insulin (or alternatively CysA10,CysB1,des-ThrB30 human insulin) is an analogue of human insulin where the amino acid in position 10 in the A chain is substituted with cysteine, the amino acid in position 1 in the B chain is substituted with cysteine, and the amino acid in position 30 (threonine, Thr) in the B chain is deleted.

Herein, the naming of the peptides or proteins is done according to the following principles: The names are given as mutations and modifications (such as acylations) relative to the parent peptide or protein such as human insulin. For the naming of the acyl moiety, the naming is done according to IUPAC nomenclature and in other cases as peptide nomenclature. For example, naming the acyl moiety:

CHEM 1

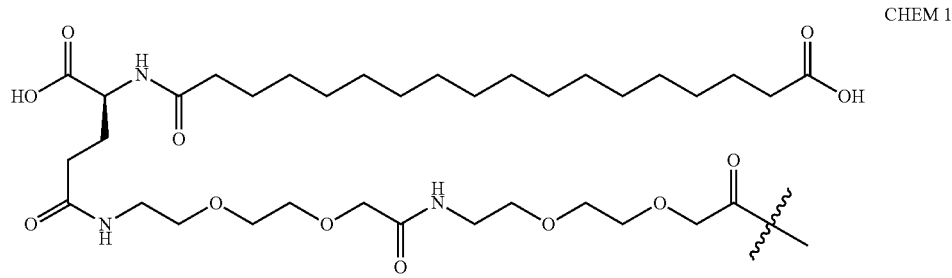 [SMILES: *C(=O)COCCOCCNC(=O)COCCOCCNC(=O)CC[C@H](NC(=O)CCCCCCCCCCCCCCCCC(=O)O)C(=O)O]

In one embodiment an insulin derivative according to the invention comprises a side chain and between 2 and 9 mutations relative to human insulin wherein at least two substitutions are to cysteine residues, alternatively an insulin derivative according to the invention comprises a side chain and between 2 and 8 mutations relative to human insulin wherein at least two substitutions are to cysteine residues, alternatively a side chain and between 2 and 7 mutations relative to human insulin wherein at least two substitutions are to cysteine residues, alternatively a side chain and between 2 and 6 mutations relative to human insulin wherein at least two substitutions are to cysteine residues, alternatively a side chain and between 2 and 5 mutations relative to human insulin wherein at least two substitutions are to cysteine residues, alternatively a side chain and between 2 and 4 mutations relative to human insulin wherein at least two substitutions are to cysteine residues, alternatively a side chain and between 2 and 3 mutations relative to human insulin wherein at least two substitutions are to cysteine residues, or alternatively a side chain and 2 cysteine substitutions relative to human insulin.

Modifications in the insulin molecule are denoted stating the chain (A or B), the position, and the one or three letter code for the amino acid residue substituting the native amino acid residue.

Herein terms like "A1", "A2" and "A3" etc. indicates the amino acid in position 1, 2 and 3 etc., respectively, in the A chain of insulin (counted from the N-terminal end). Simimay e.g. be "octadecanedioyl-γGlu-OEG-OEG", "octadecanedioyl-gGlu-OEG-OEG", "octadecanedioyl-gGlu-2xOEG", or "17-carboxyheptadecanoyl-γGlu-OEG-OEG", wherein OEG is short hand notation for the amino acid residue, 8-amino-3,6-dioxaoctanoic acid, —NH(CH$_2$)$_2$—O—(CH$_2$)$_2$ OCH$_2$CO—, and γGlu (or gGlu) is short hand notation for the amino acid gamma L-glutamic acid moiety.

For example, the insulin of example 1 (with the sequence/structure given below) is named "A10C, A14E, B4C, B25H, B29K(N$^\epsilon$Octadecanedioyl-gGlu-OEG-OEG), desB30 human insulin" to indicate that the amino acid in position A10, I in human insulin, has been mutated to C; A14, Y in human insulin, has been mutated to E; the amino acid in position B4, Q in human insulin, has been mutated to C; the amino acid in position B25, F in human insulin, has been mutated to H, the amino acid in position B29, K as in human insulin, has been modified by acylation on the epsilon nitrogen in the lysine residue of B29, denoted N$^\epsilon$, by the residue octadecanedioyl-γGlu-OEG-OEG, and the amino acid in position B30, T in human insulin, has been deleted. Asterisks in the formula below indicate that the residue in question is different (i.e. mutated) as compared to human insulin. The disulfide bonds as found in human insulin are shown with sulphur atoms, and the additional disulfide bond of the invention is shown with a line.

CHEM 2

SEQ. ID. NO: 1

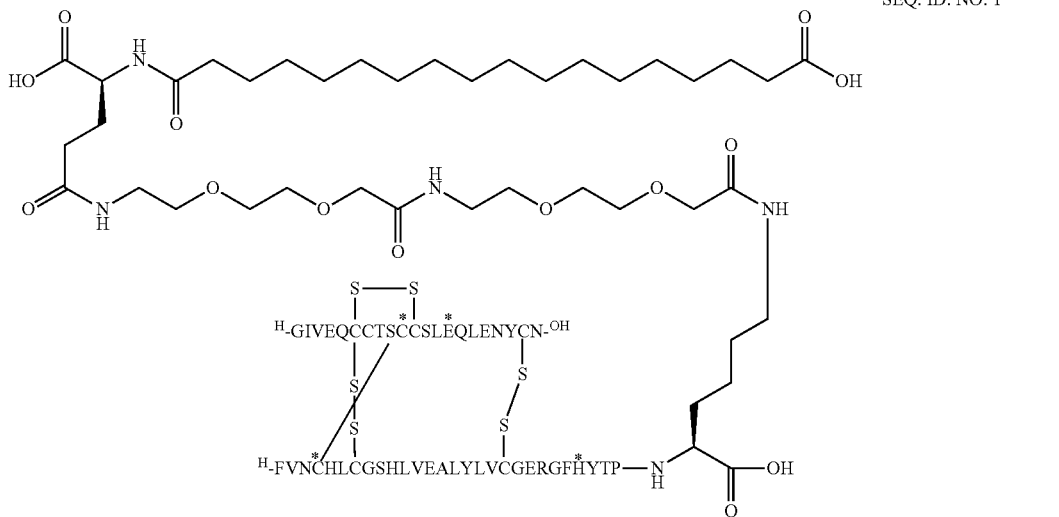

In addition, the insulins of the invention may also be named according to IUPAC nomenclature (OpenEye, IUPAC style). According to this nomenclature, the above acylated insulin with an additional disulfide bridge is assigned the following name:
N{Epsilon-B29}-[2-[2-[2-[[2-[2-[2-[[(4S)-4-carboxy-4-(17-carboxyheptadecanoylamino)butanoyl]amino]ethoxy]ethoxy]-acetyl]amino]ethoxy]ethoxy]acetyl]-[CysA10, GluA14,CysB4,HisB25],des-ThrB30-Insulin(human).

Herein, the term "amino acid residue" is an amino acid from which a hydroxy group has been removed from a carboxy group and/or from which a hydrogen atom has been removed from an amino group.

In one aspect of the invention, the insulin derivative according to the invention comprises an acyl group on e.g. the ε-amino group of a Lys residue of the insulin amino acid sequence. In one aspect the insulin derivative comprises an albumin binding residue, i.e. a residue which under in vivo conditions binds to albumin when attached to a peptide or protein.

In one aspect, the albumin binding residue is a lipophilic residue. In a further aspect, the lipophilic residue is attached to the insulin amino acid sequence via a linker.

In a further aspect of the invention, the albumin binding residue is negatively charged at physiological pH. In another aspect of the invention, the albumin binding residue comprises a group which can be negatively charged. One preferred group which can be negatively charged is a carboxylic acid group.

In one aspect, the albumin binding residue is an α,ω-fatty diacid residue.

In a further aspect of the invention, the α,ω-fatty diacid residue of the lipophilic residue has from 6 to 40 carbon atoms, from 8 to 26 carbon atoms or from 8 to 22 carbon atoms, or from 14 to 22 carbon atoms, or from 16 to 22 carbon atoms, or from 16 to 20 carbon atoms, or from 16 to 18 carbon atoms, or 16 carbon atoms, or 18 carbon atoms, or 20 carbon atoms, or 22 carbon atoms.

In another aspect of the invention, the albumin binding residue is an acyl group of a straight-chain or branched alkane α,ω-dicarboxylic acid. In a further aspect the albumin binding residue is an acyl group of a straight-chain or branched alkane α,ω-dicarboxylic acid which includes an amino acid portion such as e.g. a gamma-Glu portion. In yet a further aspect the albumin binding residue is an acyl group of a straight-chain or branched alkane α,ω-dicarboxylic acid which includes two amino acid portions such as e.g. a gamma-Glu portion and a 8-amino-3,6-dioxaoctanoic acid (OEG) portion. In yet a further aspect the albumin binding residue is an acyl group of a straight-chain or branched alkane am-dicarboxylic acid which includes more amino acid portions such as e.g. one gamma-Glu portion and consecutive 8-amino-3,6-dioxaoctanoic acid (OEG) portions.

In one embodiment, the acyl moiety attached to the parent insulin analogue has the general formula:

$$\text{Acy-AA1}_n\text{-AA2}_m\text{-AA3}_p \qquad \text{CHEM 3}$$

wherein n is 0 or an integer in the range from 1 to 3; m is 0 or an integer in the range from 1 to 10; p is 0 or an integer in the range from 1 to 10; Acy is a fatty acid or a fatty diacid comprising from about 8 to about 24 carbon atoms; AA1 is a neutral linear or cyclic amino acid residue; AA2 is an acidic amino acid residue; AA3 is a neutral, alkyleneglycol-containing amino acid residue; the order by which AA1, AA2 and AA3 appears in the formula can be interchanged independently; AA2 can occur several times along the formula (e.g., Acy-AA2-AA3$_2$-AA2-); AA2 can occur independently (=being different) several times along the formula (e.g., Acy-AA2-AA3$_2$-AA2-); the connections between Acy, AA1, AA2 and/or AA3 are amide (peptide) bonds which, formally, can be obtained by removal of a hydrogen atom or a hydroxyl group (water) from each of Acy, AA1, AA2 and AA3; and attachment to the protease stabilised insulin can be from the C-terminal end of a AA1, AA2, or AA3 residue in the acyl moiety of the formula (I) or from one of the side chain(s) of an AA2 residue present in the moiety of formula (I).

In another embodiment, the acyl moiety attached to the parent insulin analogue has the general formula Acy-AA1$_n$-AA2$_m$-AA3$_p$-(I), wherein AA1 is selected from Gly, D- or L-Ala, βAla, 4-aminobutyric acid, 5-aminovaleric acid, 6-aminohexanoic acid, D- or L-Glu-α-amide, D- or L-Glu-γ-amide, D- or L-Asp-α-amide, D- or L-Asp-β-amide, or a group of one of the formula:

CHEM 4

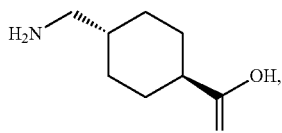

(tranexamic acid (Trx))

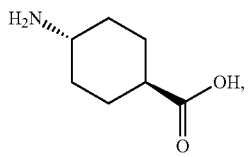

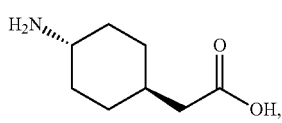

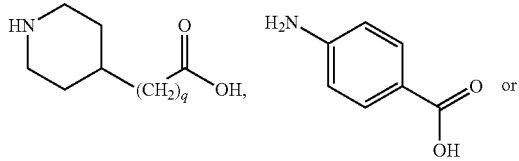

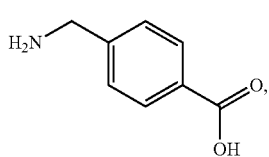

from which a hydrogen atom and/or a hydroxyl group has been removed and wherein q is 0, 1, 2, 3 or 4 and, in this embodiment, AA1 may, alternatively, be 7-aminoheptanoic acid or 8-aminooctanoic acid.

In another embodiment, the acyl moiety attached to the parent insulin analogue has the general formula Acy-AA1$_n$-AA2$_m$-AA3$_p$-(I), wherein AA1 is as defined above and AA2 is selected from L- or D-Glu, L- or D-Asp, L- or D-homoGlu or any of the following:

CHEM 5

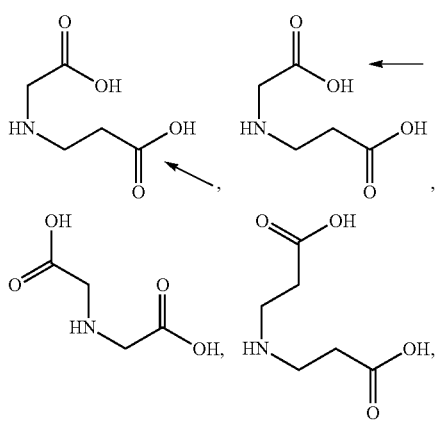

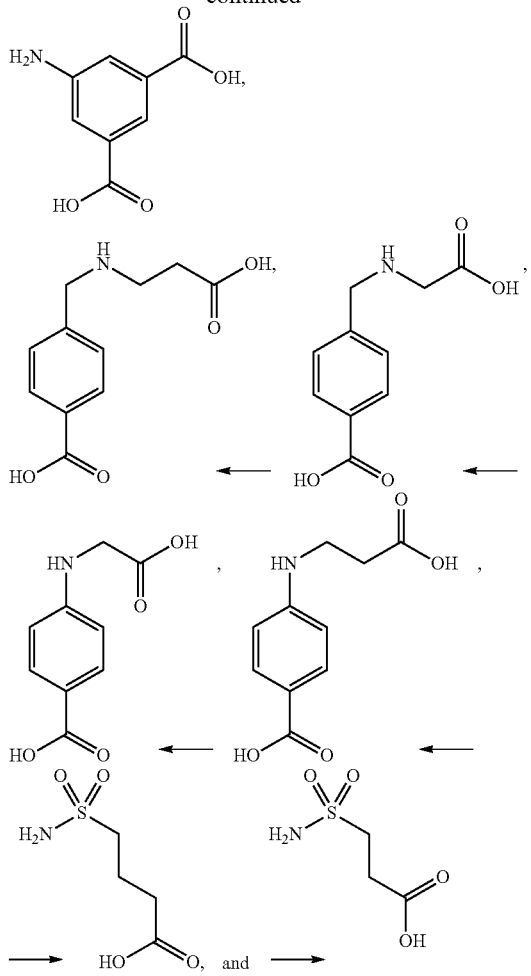

from which a hydrogen atom and/or a hydroxyl group has been removed and wherein the arrows indicate the attachment point to the amino group of AA1, AA2, AA3, or to the amino group of the protease stabilised insulin.

In one aspect, the neutral cyclic amino acid residue designated AA1 is an amino acid containing a saturated 6-membered carbocyclic ring, optionally containing a nitrogen hetero atom, and preferably the ring is a cyclohexane ring or a piperidine ring. Preferably, the molecular weight of this neutral cyclic amino acid is in the range from about 100 to about 200 Da.

The acidic amino acid residue designated AA2 is an amino acid with a molecular weight of up to about 200 Da comprising two carboxylic acid groups and one primary or secondary amino group. Alternatively, acidic amino acid residue designated AA2 is an amino acid with a molecular weight of up to about 250 Da comprising one carboxylic acid group and one primary or secondary sulphonamide group.

The neutral, alkyleneglycol-containing amino acid residue designated AA3 is an alkyleneglycol moiety, optionally an oligo- or polyalkyleneglycol moiety containing a carboxylic acid functionality at one end and a amino group functionality at the other end.

Herein, the term alkyleneglycol moiety covers mono-alkyleneglycol moieties as well as oligo-alkyleneglycol moieties. Mono- and oligoalkyleneglycols comprises monoand oligoethyleneglycol based, mono- and oligopropyleneglycol based and mono- and oligobutyleneglycol based chains, i.e., chains that are based on the repeating unit —CH$_2$CH$_2$O—, —CH$_2$CH$_2$CH$_2$O— or —CH$_2$CH$_2$CH$_2$CH$_2$O—. The alkyleneglycol moiety is monodisperse (with well defined length/molecular weight). Monoalkyleneglycol moieties comprise —OCH$_2$CH$_2$O—, —OCH$_2$CH$_2$CH$_2$O— or —OCH$_2$CH$_2$CH$_2$CH$_2$O— containing different groups at each end.

As mentioned herein, the order by which AA1, AA2 and AA3 appears in the acyl moiety with the formula (I) (Acy-AA1$_n$-AA2$_n$-AA3$_p$-) can be interchanged independently. Consequently, the formula Acy-AA1$_n$-AA2$_n$-AA3$_p$- also covers moieties like, e.g., the formula Acy-AA2$_n$-AA1$_n$-AA3$_p$—, the formula Acy-AA2-AA3$_n$-AA2-, and the formula Acy-AA3$_p$-AA2$_m$-AA1$_n$-, wherein Acy, AA1, AA2, AA3, n, m and p are as defined herein.

As mentioned herein, the connections between the moieties Acy, AA1, AA2 and/or AA3 are formally obtained by amide bond (peptide bond) formation (—CONH—) by removal of water from the parent compounds from which they formally are build. This means that in order to get the complete formula for the acyl moiety with the formula (I) (Acy-AA1$_n$-AA2$_n$-AA3$_p$-, wherein Acy, AA1, AA2, AA3, n, m and p are as defined herein), one has, formally, to take the compounds given for the terms Acy, AA1, AA2 and AA3 and remove a hydrogen and/or hydroxyl from them and, formally, to connect the building blocks so obtained at the free ends so obtained.

Non-limiting, specific examples of the acyl moieties of the formula Acy-AA1$_n$-AA2$_m$, AA3$_p$- which may be present in the acylated insulin analogues of this invention are listed in WO 2009/115469 A1, pp. 27-43:

Any of the above non-limiting specific examples of acyl moieties of the formula Acy-AA1$_n$-AA2$_n$-AA3$_p$- can be attached to an epsilon amino group of a lysine residue present in any of the above non-limiting specific examples of parent insulin analogues thereby giving further specific examples of acylated insulin analogues of this invention.

The parent insulin analogues can be converted into the acylated insulins containing additional disulfide bonds of this invention by introducing of the desired group of the formula Acy-AA1$_n$-AA2$_n$-AA3$_p$- in the lysine residue. The desired group of the formula Acy-AA1$_n$-AA2$_n$-AA3$_p$- can be introduced by any convenient method and many methods are disclosed in the prior art for such reactions. More details appear from the examples herein.

In one aspect of the invention, the sites of cysteine substitutions are chosen in such a way that the human insulin derivative retains the desired biological activities associated with human insulin. Desired biological activities are known to the person skilled in the art and e.g. include binding to the insulin receptor, binding to the IGF-1 (Insulin Growth Factor 1) receptor, in vitro potency, in vivo potency as e.g. described in the Examples 106 and 107.

In one aspect, insulin derivatives according to the invention are obtained, wherein the receptor binding to the insulin receptor is at least 1% of the receptor binding of insulin derivative without one or more additional disulfide bonds to the insulin receptor. In one aspect, the receptor binding to the insulin receptor is at least 3% of the receptor binding of insulin derivative without one or more additional disulfide bonds to the insulin receptor. In one aspect, the receptor binding to the insulin receptor is at least 5% of the receptor binding of insulin derivative without one or more additional disulfide bonds to the insulin receptor. In one aspect, the receptor binding to the insulin receptor is at least 10% of the receptor binding of insulin derivative without one or more additional disulfide bonds to the insulin receptor. In one aspect, the receptor binding to the insulin receptor is at least 15% of the receptor binding of insulin derivative without one or more additional disulfide bonds to the insulin receptor. In one aspect, the receptor binding to the insulin receptor is at least 20% of the receptor binding of insulin derivative without one or more additional disulfide bonds to the insulin receptor.

In one aspect, insulin derivatives according to the invention are obtained, wherein the receptor binding to the insulin receptor is increased. In one aspect, insulin derivatives according to the invention are obtained, wherein the receptor binding to the insulin receptor is at least 110% of the receptor binding of insulin derivative without one or more additional disulfide bonds to the insulin receptor. In one aspect, the receptor binding to the insulin receptor is at least 120% of the receptor binding of insulin derivative without one or more additional disulfide bonds to the insulin receptor. In one aspect, the receptor binding to the insulin receptor is at least 130% of the receptor binding of insulin derivative without one or more additional disulfide bonds to the insulin receptor. In one aspect, the receptor binding to the insulin receptor is at least 140% of the receptor binding of insulin derivative without one or more additional disulfide bonds to the insulin receptor. In one aspect, the receptor binding to the insulin receptor is at least 150% of the receptor binding of insulin derivative without one or more additional disulfide bonds to the insulin receptor. In one aspect, the receptor binding to the insulin receptor is at least 160% of the receptor binding of insulin derivative without one or more additional disulfide bonds to the insulin receptor. In one aspect, the receptor binding to the insulin receptor is between 110 and 200% of the receptor binding of insulin derivative without one or more additional disulfide bonds to the insulin receptor. In one aspect, the receptor binding to the insulin receptor is between 120 and 180% of the receptor binding of insulin derivative without one or more additional disulfide bonds to the insulin receptor. In one aspect, the receptor binding to the insulin receptor is between 140 and 180% of the receptor binding of insulin derivative without one or more additional disulfide bonds to the insulin receptor. In one aspect, the receptor binding to the insulin receptor is between 150 and 170% of the receptor binding of insulin derivative without one or more additional disulfide bonds to the insulin receptor.

The production of polypeptides, e.g., insulins, is well known in the art. An insulin analogue to be used for producing an insulin derivative according to the invention may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999. The insulin analogue may also be produced by a method which comprises culturing a host cell containing a DNA sequence encoding the analogue and capable of expressing the insulin analogue in a suitable nutrient medium under conditions permitting the expression of the insulin analogue. Several recombinant methods may be used in the production of human insulin and human insulin analogues. Three non-limiting examples of methods which may be used in the production of insulin in microorganisms such as, e.g., *Escherichia coli* and *Saccharomyces cerevisiae* are, e.g., disclosed in WO2008034881.

Typically, the insulin analogue is produced by expressing a DNA sequence encoding the insulin analogue in question or a precursor thereof in a suitable host cell by well known technique as disclosed in e.g. EP 1,246,845 or WO2008034881 both of which patents are herein specifically incorporated by reference.

The insulin analogue may be expressed with an N-terminal extension as disclosed in EP 1,246,845. After secretion to the culture medium and recovery, the insulin precursor will be subjected to various in vitro procedures to remove the possible N-terminal extension sequence and connecting peptide to give the insulin analogue. Such methods include enzymatic conversion by means of trypsin or an *Achromobacter lyticus* protease in the presence of an L-threonine ester followed by conversion of the threonine ester of the insulin analogue into the insulin analogue by basic or acid hydrolysis as described in U.S. Pat. Nos. 4,343,898 or 4,916,212

Examples of N-terminal extensions of the type suitable in the present invention are disclosed in U.S. Pat. No. 5,395, 922 and EP patent No. 765,395 both of which patents are herein specifically incorporated by reference.

For insulin analogues comprising non-natural amino acid residues, the recombinant cell should be modified such that the non-natural amino acids are incorporated into the analogue, for instance by use of tRNA mutants. Hence, briefly, the insulin analogues according to the invention are prepared analogously to the preparation of known insulin analogues.

In still a further embodiment, the invention relates to a process for producing an insulin derivative comprising:
(i) culturing a host cell comprising a nucleic acid sequence encoding an insulin precursor;
(ii) isolating the insulin precursor from the culture medium;
(iii) converting the insulin precursor into an insulin analogue by in vitro enzymatic conversion; and
(iv) acylating the insulin analogue with a side chain.

In still a further embodiment, the invention relates to a process for producing an insulin derivative comprising:
(i) culturing a host cell comprising a nucleic acid sequence encoding an insulin precursor;
(ii) isolating the insulin precursor from the culture medium;
(iii) converting the insulin precursor into an insulin analogue; and
(iv) acylating the insulin analogue with a side chain.

In one embodiment of the present invention the host cell is a yeast host cell and in a further embodiment the yeast host cell is selected from the genus *Saccharomyces*. In a further embodiment the yeast host cell is selected from the species *Saccharomyces cerevisiae*.

Insulin analogues may be modified, such as acylated, according to methods known to the person skilled in the art as e.g. described in WO 2010/029159, WO 00/55119, WO 04/029077 and WO 2006/008238, which are incorporated by reference.

In one aspect of the invention a method for stabilizing an insulin derivative is obtained which comprises substituting two or more amino acids of an insulin derivative with cysteine residues, wherein
 a. the three disulfide bonds of human insulin are retained and
 b. the sites of cysteine substitutions are chosen in such a way that the introduced cysteine residues are placed in the three dimensional structure of the folded insulin analogue to allow for the formation of one or more additional disulfide bonds not present in human insulin,
thereby creating a human insulin derivative comprising one or more additional disulfide bonds not present in human insulin.

It is apparent from the description how to obtain an insulin derivative according to the invention. The person skilled in the art thus knows when reading the description how to modify an insulin derivative in such a way that the introduced cysteine residues are placed in the three dimensional structure of the folded insulin analogue to allow for the formation of one or more additional disulfide bonds not present in human insulin in addition to the three disulfide bonds of human insulin.

Pharmaceutical Compositions

Another object of the present invention is to provide a pharmaceutical formulation comprising an insulin derivative according to the present invention which is present in a concentration from 0.1 mg/ml to 500 mg/ml, and wherein said formulation has a pH from 2.0 to 10.0. The formulation may further comprise protease inhibitor(s), a buffer system, preservative(s), tonicity agent(s), chelating agent(s), stabilizers and surfactants. In one embodiment of the invention the pharmaceutical formulation is an aqueous formulation, i.e. formulation comprising water.

In another embodiment the pharmaceutical formulation is a dried formulation (e.g. freeze-dried or spray-dried) ready for use without any prior dissolution.

Pharmaceutical compositions containing an insulin derivative according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

For parenteral administration, an insulin derivative of this invention is formulated analogously with the formulation of known insulins. Furthermore, for parenterally administration, an insulin derivative of this invention is administered analogously with the administration of known insulins and the physicians are familiar with this procedure.

Parenteral administration can be performed by means of a syringe, optionally a pen-like syringe. Alternatively, parenteral administration can be performed by means of an infusion pump.

Injectable compositions containing an insulin derivative of this invention can be prepared using the conventional techniques of the pharmaceutical industry which involve dissolving and mixing the ingredients as appropriate to give the desired end product. Thus, according to one procedure, an insulin derivaitve of this invention is dissolved in an amount of water which is somewhat less than the final volume of the composition to be prepared. An isotonic agent, a preservative and a buffer is added as required and the pH value of the solution is adjusted, if necessary, using an acid, for example, hydrochloric acid, or a base, for example, aqueous sodium hydroxide, as needed. Finally, the volume of the solution is adjusted with water to give the desired concentration of the ingredients.

More precisely, an insulin derivative preparation of this invention, for example a solution or suspension, may be prepared by dissolving a compound of this invention in an aqueous medium at slightly acidic conditions, for example, in a concentration in the range from about 240 to about 2400 nmole/ml. The aqueous medium is made isotonic, for example, with sodium chloride or glycerol. Furthermore, the aqueous medium may contain buffers such as acetate or citrate, preservatives such as m-cresol or phenol and zinc ions, for example, in a concentration of up to about 20 μg of $Zn^{++}$ per unit of insulin activity. The pH value of the solution is adjusted towards neutrality without getting too close to the isoelectric point of the compound of this invention in order to avoid precipitation. The pH value of the final insulin preparation depends upon which compound of this invention is used, the concentration of zinc ions and the concentration of the compound of this invention. The insulin derivative preparation is made sterile, for example, by sterile filtration.

Formulations intended for oral use may be prepared according to any known method, and such formulations may contain one or more agents selected from the group consisting of sweetening agents, flavouring agents, colouring agents, and preserving agents in order to provide pharmaceutically elegant and palatable preparations. Tablets may contain the active ingredient in a mixture with non-toxic pharmaceutically-acceptable excipients which are suitable for the manufacture of tablets. These excipients may be for example, inert diluents, such as mannitol, maltodextrin, kaolin, calcium carbonate, sodium carbonate, lactose, calcium phosphate or sodium phosphate; granulating and disintegrating agents, for example corn starch; binding agents, for example, starch, gelatine, polymers or acacia; and lubricating agents, for example magnesium stearate, stearic acid or talc. The tablets may be uncoated or they may be coated by known techniques to delay disintegration or release of the therapeutically active polypeptide.

The orally administerable formulations of the present invention may be prepared and administered according to methods well known in pharmaceutical chemistry, see Remington's Pharmaceutical Sciences, $17^{th}$ ed. (A. Osol ed., 1985).

The insulin derivative preparations of this invention are used similarly to the use of the known insulin preparations.

The amount of a compound of this invention to be administered, the determination of how frequently to administer a compound of this invention, and the election of which compound or compounds of this invention to administer, optionally together with another antidiabetic compound, is decided in consultation with a practitioner who is familiar with the treatment of diabetes.

In one aspect, the insulin derivative according to the invention is administered orally. In one aspect, the insulin derivative according to the invention is administered parentally.

In another embodiment, the present invention relates to an insulin derivative according to the invention for use as a medicament.

In one embodiment, an insulin derivative according to the invention is used for the preparation of a medicament for the treatment or prevention of hyperglycemia, type 2 diabetes, impaired glucose tolerance and type 1 diabetes.

In another embodiment, an insulin derivative according to the invention is used as a medicament for delaying or preventing disease progression in type 2 diabetes.

In one embodiment of the invention, the insulin derivative according to the invention is for use as a medicament for the treatment or prevention of hyperglycemia, type 2 diabetes, impaired glucose tolerance, type 1 diabetes or for delaying or preventing disease progression in type 2 diabetes.

In a further embodiment of the invention, a method for the treatment or prevention of hyperglycemia, type 2 diabetes, impaired glucose tolerance, type 1 diabetes or for delaying or preventing disease progression in type 2 diabetes, the method comprising administering to a patient in need of such treatment an effective amount for such treatment of an insulin derivative according to the invention, is provided.

The term "diabetes" includes type 1 diabetes, type 2 diabetes and other states that cause hyperglycaemia.

The term "treatment" of a disease includes treatment, prevention or alleviation of the disease.

The Following is a List of Aspects Further Describing the Invention:

1. An insulin derivative having two or more cysteine substitutions and a side-chain attached to the insulin, where the three disulfide bonds of human insulin are retained, and
   the sites of cysteine substitutions are chosen in such a way that the introduced cysteine residues are placed in the three dimensional structure of the folded insulin derivative to allow for the formation of one or more additional disulfide bonds not present in human insulin.
2. An insulin derivative according to aspect 1, wherein the sites of cysteine substitutions are chosen in such a way that
   (1) the introduced cysteine residues are placed in the three dimensional structure of the folded insulin derivative to allow for the formation of one or more additional disulfide bonds not present in human insulin, and
   (2) the human insulin derivative retains the desired biological activities associated with human insulin.
3. An insulin derivative according to aspect 1 or 2, wherein the sites of cysteine substitutions are chosen in such a way that
   (1) the introduced cysteine residues are placed in the three dimensional structure of the folded insulin derivative to allow for the formation of one or more additional disulfide bonds not present in human insulin,
   (2) the human insulin derivative retains the desired biological activities associated with human insulin, and
   (3) the human insulin derivative has increased physical stability relative to human insulin and/or parent insulin
4. An insulin derivative according to any one of the preceding aspects, wherein the sites of cysteine substitutions are chosen in such a way that
   (1) the introduced cysteine residues are placed in the three dimensional structure of the folded insulin derivative to allow for the formation of one or more additional disulfide bonds not present in human insulin,
   (2) the human insulin derivative retains the desired biological activities associated with human insulin, and
   (3) the human insulin derivative is stabilized against proteolytic degradation.
5. An insulin derivative according to any one of the preceding aspects, to the extend possible, wherein at least one amino acid residue in a position selected from the group consisting of A9, A10, A11 and A12 of the A-chain is substituted with a cysteine, at least one amino acid residue in a position selected from the group consisting of B1, B2, B3, B4, B5 and B6 of the B-chain is substituted with a cysteine and optionally the amino acid in position B30 is deleted.

6. An insulin derivative according to any one of the preceding aspects, to the extend possible, wherein the amino acid residue in position A10 of the A-chain is substituted with a cysteine, the amino acid residue in a position selected from the group consisting of B1, B2, B3 and B4 of the B-chain is substituted with a cysteine, and optionally the amino acid in position B30 is deleted.

7. An insulin derivative according to any one of the preceding aspects, to the extend possible, wherein the amino acid residue in position A10 of the A-chain is substituted with a cysteine, the amino acid residue in a position selected from the group consisting of B3 and B4 of the B-chain is substituted with a cysteine, and optionally the amino acid in position B30 is deleted.

8. An insulin derivative according to any one of the preceding aspects, to the extend possible, wherein the amino acid residue in position A10 of the A-chain is substituted with a cysteine, and amino acid in position B3 of the B-chain is substituted with a cysteine, and optionally the amino acid in position B30 is deleted.

9. An insulin derivative according to any one of the preceding aspects, to the extend possible, wherein the amino acid residue in position A10 of the A-chain is substituted with a cysteine, the amino acid in position B4 of the B-chain is substituted with a cysteine, and optionally the amino acid in position B30 is deleted.

10. An insulin derivative according to any one of the preceding aspects wherein the amino acid residue in position A21 of the A-chain is substituted with a cysteine, the amino acid residue in a position selected from the group consisting of B25 and B26 of the B-chain is substituted with a cysteine, and optionally the amino acid in position B30 is deleted.

11. An insulin derivative according to any one of the preceding aspects, to the extend possible, wherein the amino acid residue in position A10 of the A-chain is substituted with a cysteine, the amino acid residue in a position selected from the group consisting of B1, B2, B3 and B4 of the B-chain is substituted with a cysteine, and optionally the amino acid in position B30 is deleted,
wherein the elimination half-life of the insulin derivative is extended relative to an insulin derivative without one or more additional disulfide bonds.

12. An insulin derivative according to any one of the preceding aspects, to the extend possible, wherein the amino acid residue in position A10 of the A-chain is substituted with a cysteine, the amino acid residue in a position selected from the group consisting of B3 and B4 of the B-chain is substituted with a cysteine, and optionally the amino acid in position B30 is deleted,
wherein the elimination half-life of the insulin derivative is extended relative to an insulin derivative without one or more additional disulfide bonds.

13. An insulin derivative according to any one of the preceding aspects, to the extend possible, wherein the amino acid residue in position A10 of the A-chain is substituted with a cysteine, and amino acid in position B3 of the B-chain is substituted with a cysteine, and optionally the amino acid in position B30 is deleted,
wherein the elimination half-life of the insulin derivative is extended relative to an insulin derivative without one or more additional disulfide bonds.

14. An insulin derivative according to any one of the preceding aspects, to the extend possible, wherein the amino acid residue in position A10 of the A-chain is substituted with a cysteine, the amino acid in position B4 of the B-chain is substituted with a cysteine, and optionally the amino acid in position B30 is deleted,
wherein the elimination half-life of the insulin derivative is extended relative to an insulin derivative without one or more additional disulfide bonds.

15. An insulin derivative according to any one of the preceding aspects wherein the amino acid residue in position A21 of the A-chain is substituted with a cysteine, the amino acid residue in a position selected from the group consisting of B25 and B26 of the B-chain is substituted with a cysteine, and optionally the amino acid in position B30 is deleted,
wherein the elimination half-life of the insulin derivative is extended relative to an insulin derivative without one or more additional disulfide bonds.

16. An insulin derivative according to any one of the preceding aspects, to the extend possible, wherein one or more additional disulfide bonds are obtained between the A-chain and the B-chain 17. An insulin derivative according to any one of the preceding aspects, to the extend possible, wherein one or more additional disulfide bonds are obtained between the A-chain and the B-chain 18. An insulin derivative according to any one of the preceding aspects, to the extend possible, wherein at least one additional disulfide bond is connecting two cysteines in the A-chain or connecting two cysteines in the B-chain.

19. An insulin derivative according to any one of the preceding aspects, to the extend possible, wherein the receptor binding to the insulin receptor is at least 1% of the receptor binding of an insulin derivative without one or more additional disulfide bonds.

20. An insulin derivative according to any one of the preceding aspects, to the extend possible, wherein the receptor binding to the insulin receptor is at least 25% of the receptor binding of an insulin derivative without one or more additional disulfide bonds.

21. An insulin derivative according to any one of the preceding aspects, to the extend possible, wherein the receptor binding to the insulin receptor is at least 50% of the receptor binding of an insulin derivative without one or more additional disulfide bonds.

22. An insulin derivative according to any one of the preceding aspects, to the extend possible, wherein the receptor binding to the insulin receptor is at least 75% of the receptor binding of an insulin derivative without one or more additional disulfide bonds.

23. An insulin derivative according to any one of the preceding aspects, to the extend possible, wherein the receptor binding to the insulin receptor is at least 90% of the receptor binding of an insulin derivative without one or more additional disulfide bonds.

24. An insulin derivative according to any one of the preceding aspects, to the extend possible, which has improved physical stability relative to the parent insulin.

25. An insulin derivative according to any one of the preceding aspects, to the extend possible, which has a more protracted profile than an insulin derivative without one or more additional disulfide bonds.

26. An insulin derivative according to any one of the preceding aspects, to the extend possible, which has an extended elimination half-life relative to an insulin derivative without one or more additional disulfide bonds.

27. An insulin derivative according to any one of the preceding aspects, to the extend possible, wherein the amino acid in position B30 is deleted.
28. An insulin derivative according to any one of the preceding aspects, to the extend possible, wherein at least one additional disulfide bond is connecting two cysteines in the A-chain or connecting cysteines in the B-chain
29. An insulin derivative according to any one of the preceding aspects, to the extend possible, which has two cysteine substitutions.
30. An insulin derivative according to any one of the preceding aspects, to the extend possible, wherein the insulin is selected from the group consisting of:
A10C, A14E, B1C, B16H, B25H, desB30 human insulin,
A10C, A14E, B1C, B25H, desB30 human insulin,
A10C, A14E, B2C, B16H, B25H, desB30 human insulin,
A10C, A14E, B2C, B25A, desB30 human insulin,
A10C, A14E, B2C, B25H, desB30 human insulin,
A10C, A14E, B3C, B16H, B25H, desB30 human insulin,
A10C, A14E, B3C, B25H, desB27, desB30 human insulin,
A10C, A14E, B3C, B25H, desB30 human insulin,
A10C, A14E, B3C, desB27, desB30 human insulin,
A10C, A14E, B4C, B16H, B25H, desB30 human insulin,
A10C, A14E, B4C, B25A, desB30 human insulin,
A10C, A14E, B4C, B25H, B28E, desB30 human insulin,
A10C, A14E, B4C, B25H, desB27, desB30 human insulin,
A10C, A14E, B4C, B25H, desB30 human insulin,
A10C, A14E, B4C, B25N, B27E, desB30 human insulin,
A10C, A14E, B4C, B25N, desB27, desB30 human insulin,
A10C, A14E, desB1, B4C, B25H, desB30 human insulin,
A10C, A14H, B4C, B25H, desB30 human insulin,
A10C, B3C, B25H, desB27, desB30 human insulin,
A10C, B3C, B25H, desB30 human insulin,
A10C, B4C, B25H, desB27, desB30 human insulin,
A10C, B4C, B25H, desB30 human insulin,
A10C, A14E, B1C, B16H, B25H, desB30 human insulin,
A10C, A14E, B2C, B16H, B25H, desB30 human insulin,
A10C, A14E, B3C, B16H, B25H, desB30 human insulin,
A10C, A14E, B4C, B16H, B25H, desB30 human insulin
and a sidechain is attached to the N-terminal of the insulin or the epsilon amino group of a lysine residue in the insulin,
31. An insulin derivative according to any one of the preceding aspects, to the extend possible, wherein the insulin is selected from the group consisting of:
A10C, A14E, B1C, B16H, B25H, desB30 human insulin,
A10C, A14E, B1C, B25H, desB30 human insulin,
A10C, A14E, B2C, B16H, B25H, desB30 human insulin,
A10C, A14E, B2C, B25A, desB30 human insulin,
A10C, A14E, B2C, B25H, desB30 human insulin,
A10C, A14E, B3C, B16H, B25H, desB30 human insulin,
A10C, A14E, B3C, B25H, desB27, desB30 human insulin,
A10C, A14E, B3C, B25H, desB30 human insulin,
A10C, A14E, B3C, desB27, desB30 human insulin,
A10C, A14E, B4C, B16H, B25H, desB30 human insulin,
A10C, A14E, B4C, B25A, desB30 human insulin,
A10C, A14E, B4C, B25H, B28E, desB30 human insulin,
A10C, A14E, B4C, B25H, desB27, desB30 human insulin,
A10C, A14E, B4C, B25H, desB30 human insulin,
A10C, A14E, B4C, B25N, B27E, desB30 human insulin,
A10C, A14E, B4C, B25N, desB27, desB30 human insulin,
A10C, A14E, desB1, B4C, B25H, desB30 human insulin,
A10C, A14H, B4C, B25H, desB30 human insulin,
A10C, B3C, B25H, desB27, desB30 human insulin,
A10C, B3C, B25H, desB30 human insulin,
A10C, B4C, B25H, desB27, desB30 human insulin,
A10C, B4C, B25H, desB30 human insulin,
A10C, A14E, B1C, B16H, B25H, desB30 human insulin,
A10C, A14E, B2C, B16H, B25H, desB30 human insulin,
A10C, A14E, B3C, B16H, B25H, desB30 human insulin,
A10C, A14E, B4C, B16H, B25H, desB30 human insulin
and a sidechain is attached to the epsilon amino group of a lysine residue in the B-chain of the insulin,
32. An insulin derivative any one of the preceding aspects, to the extend possible, wherein the insulin is selected from the group consisting of:
A10C, A21G, I31G, B3C, B27E, desB30 human insulin
A10C, A21G, I31G, B3E, B4C, B27E, desB30 human insulin
A10C, A21G, B2C, B3E, B27E, B28K, desB29, desB30 human insulin
A10C, A21G, B2C, B3E, B28E, desB30 human insulin
A10C, A21G, B3C, B27E, B28K, desB29, desB30 human insulin
A10C, A21G, B3C, B28E, desB30 human insulin
A10C, A21G, B3E, B4C, B22E, B28E, desB30 human insulin
A10C, A21G, B3E, B4C, B27E, B28K, desB29, desB30 human insulin
A10C, A21G, B3E, B4C, B28E, desB30 human insulin
A10C, A21G, B3E, B4C, desB24, B28E, desB30 human insulin
A10C, A21G, B3K, B4C, B28E, desB30 human insulin
A10C, A21G, B3Q, B4C, B28D, desB30 human insulin
A10C, A21G, B3Q, B4C, B28E, desB30 human insulin
A10C, A21G, B4C, B28E, desB30 human insulin
A10C, A21G, B4C, desB30 human insulin
A10C, A21G, desB1, B2C, B3E, B27E, B28K, desB29, desB30 human insulin
A10C, A21G, desB1, B2C, B3E, B28E, desB30 human insulin
A10C, A21G, desB1, B3C, B27E, B28K, desB29, desB30 human insulin
A10C, A21G, desB1, B3C, B27E, desB30 human insulin
A10C, A21G, desB1, B3C, B28E, desB30 human insulin
A10C, A21G, desB1, B3E, B4C, B27E, B28K, desB29, desB30 human insulin
A10C, A21G, desB1, B3E, B4C, B28E, desB30 human insulin
A10C, A21G, desB1, B3E, B4C, B28E, desB30 human insulin
A10C, A22K, B3C, desB27, desB30 human insulin
A10C, B1C, B28D, desB30 human insulin
A10C, B2C, B28D, desB30 human insulin
A10C, B2C, B3A, desB30 human insulin
A10C, B2C, B3D, desB30 human insulin
A10C, B2C, B3E, desB30 human insulin
A10C, B2C, B3F, desB30 human insulin
A10C, B4C, B28D human insulin
A10C, B4C, B28D, desB30 human insulin
and a sidechain is attached to the N-terminal of the insulin or the epsilon amino group of a lysine residue in the insulin,
33. An insulin derivative any one of the preceding aspects, to the extend possible, wherein the insulin is selected from the group consisting of:
A10C, A21G, I31G, B3C, B27E, desB30 human insulin
A10C, A21G, I31G, B3E, B4C, B27E, desB30 human insulin A10C, A21G, B2C, B3E, B27E, B28K, desB29, desB30 human insulin
A10C, A21G, B2C, B3E, B28E, desB30 human insulin
A10C, A21G, B3C, B27E, B28K, desB29, desB30 human insulin
A10C, A21G, B3C, B28E, desB30 human insulin
A10C, A21G, B3E, B4C, B22E, B28E, desB30 human insulin
A10C, A21G, B3E, B4C, B27E, B28K, desB29, desB30 human insulin
A10C, A21G, B3E, B4C, B28E, desB30 human insulin
A10C, A21G, B3E, B4C, desB24, B28E, desB30 human insulin
A10C, A21G, B3K, B4C, B28E, desB30 human insulin
A10C, A21G, B3Q, B4C, B28D, desB30 human insulin
A10C, A21G, B3Q, B4C, B28E, desB30 human insulin
A10C, A21G, B4C, B28E, desB30 human insulin
A10C, A21G, B4C, desB30 human insulin
A10C, A21G, desB1, B2C, B3E, B27E, B28K, desB29, desB30 human insulin
A10C, A21G, desB1, B2C, B3E, B28E, desB30 human insulin
A10C, A21G, desB1, B3C, B27E, B28K, desB29, desB30 human insulin
A10C, A21G, desB1, B3C, B27E, desB30 human insulin
A10C, A21G, desB1, B3C, B28E, desB30 human insulin
A10C, A21G, desB1, B3E, B4C, B27E, B28K, desB29, desB30 human insulin
A10C, A21G, desB1, B3E, B4C, B28E, desB30 human insulin
A10C, A21G, desB1, B3Q, B4C, B28E, desB30 human insulin
A10C, A22K, B3C, desB27, desB30 human insulin
A10C, B1C, B28D, desB30 human insulin
A10C, B2C, B28D, desB30 human insulin
A10C, B2C, B3A, desB30 human insulin
A10C, B2C, B3D, desB30 human insulin
A10C, B2C, B3E, desB30 human insulin
A10C, B2C, B3F, desB30 human insulin
A10C, B4C, B28D human insulin
A10C, B4C, B28D, desB30 human insulin and a sidechain is attached to the epsilon amino group of a lysine residue in the B-chain of the insulin, 34. An insulin derivative any one of the preceding aspects, to the extend possible, wherein the side chain is attached to the N-terminal of the insulin or the epsilon amino group of a lysine residue in the insulin, 35. An insulin derivative any one of the preceding aspects, to the extend possible, wherein the side chain is attached to the epsilon amino group of a lysine residue in the B-chain of the insulin.

36. An insulin derivative any one of the preceding aspects, to the extend possible, wherein the side chain is an acyl moiety of the general formula: Acy-AA1$_n$-AA2$_m$-AA3$_p$-.

37. An insulin derivative any one of the preceding aspects, to the extend possible, which is selected from the group consisting of the insulin derivatives mentioned in the Examples.

38. A method for stabilizing an insulin comprising substituting two or more amino acids of an insulin with cysteine residues and attaching a side-chain to the insulin, wherein
   a. the three disulfide bonds of human insulin are retained and
   b. the sites of cysteine substitutions are chosen in such a way that the introduced cysteine residues are placed in the three dimensional structure of the folded insulin derivative to allow for the formation of one or more additional disulfide bonds not present in human insulin, thereby creating an insulin derivative comprising one or more additional disulfide bonds not present in human insulin.

39. A pharmaceutical composition comprising a biologically active amount of the insulin derivative according to any one of the aspects 1-37 and a pharmaceutically acceptable carrier.

40. A pharmaceutical composition according to aspect 39 which further comprises a pharmaceutical acceptable carrier and/or excipient, and optionally an adjuvant.

41. A method for the treatment of diabetes mellitus in a subject comprising administering to a subject an insulin derivative according to any one of the aspects 1-37 or a pharmaceutical composition according to any one of the aspects 39-40.

42. A method of reducing the blood glucose level in mammals by administrating to a patient in need of such treatment a therapeutically active dose of an insulin derivative according to any one of the aspects 1-37 or a pharmaceutical composition according to any one of the aspects 39-40.

43. An insulin derivative according to any one of the aspects 1-37 for use as a pharmaceutical in the treatment or prevention of hyperglycemia, type 2 diabetes, impaired glucose tolerance and type 1 diabetes.

44. An insulin derivative according to any one of the aspects 1-37 for use as a pharmaceutical in delaying or preventing disease progression in type 2 diabetes.

45. A process for preparing a pharmaceutical composition according to any one of the aspects 39-40 comprising mixing an insulin derivative according to any one of the aspects 1-37 with pharmaceutically acceptable substances and/or excipients.

46. A pharmaceutical composition obtainable by the process according to aspect 45.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

The following examples are offered by way of illustration, not by limitation.

The abbreviations used herein are the following: βAla is beta-alanyl, Aoc is 8-aminooctanoic acid, tBu is tert-butyl, DCM is dichloromethane, DIC is diisopropylcarbodiimide, DIPEA=DIEA is N,N-disopropylethylamine, DMF is N,N-dmethylformamide, DMSO is dimethyl sulphoxide, EtOAc is ethyl acetate, Fmoc is 9-fluorenylmethyloxycarbonyl, γGlu is gamma L-glutamyl, HCl is hydrochloric acid, HOBt is 1-hydroxybenzotriazole, NMP is N-methylpyrrolidone, MeCN is acetonitrile, OEG is [2-(2-aminoethoxy)ethoxy]ethylcarbonyl, Su is succinimidyl-1-yl=2,5-dioxopyrrolidin-1-yl, OSu is succinimidyl-1-yloxy=2,5-dioxo-pyrrolidin-1-yloxy, RPC is reverse phase chromatography, RT is room temperature, TFA is trifluoroacetic acid, THF is tetrahydrofuran, TNBS is 2,4,6-trinitrobenzenesulfonic acid, TRIS is tris(hydroxymethyl)-aminomethane and TSTU is O-(N-succinimidyl)-1,1,3,3-tetramethyluronium tetrafluoroborate.

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of compounds of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

The compounds of the invention can be purified by employing one or more of the following procedures which are typical within the art. These procedures can—if needed—be modified with regard to gradients, pH, salts, concentrations, flow, columns and so forth. Depending on factors such as impurity profile, solubility of the insulins in question etcetera, these modifications can readily be recognised and made by a person skilled in the art.

After acidic HPLC or desalting, the compounds are isolated by lyophilisation of the pure fractions.

After neutral HPLC or anion exchange chromatography, the compounds are desalted, e.g. by size exclusion chromatography, precipitated at isoelectrical pH, or desalted by acidic HPLC.

Typical Purification Procedures:

The HPLC system is a Gilson system consisting of the following: Model 215 Liquid handler, Model 322-H2 Pump and a Model 155 UV Dector. Detection is typically at 210 nm and 280 nm.

The Äkta Purifier FPLC system (Amersham Biosciences) consists of the following: Model P-900 Pump, Model UV-900 UV detector, Model pH/C-900 pH and conductivity detector, Model Frac-950 Frction collector. UV detection is typically at 214 nm, 254 nm and 276 nm.

Acidic HPLC:
Column: Macherey-Nagel SP 250/21 Nucleusil 300-7 C4
Flow: 8 ml/min
Buffer A: 0.1% TFA in acetonitrile
Buffer B: 0.1% TFA in water.
Gradient: 0.0-5.0 min: 10% A
5.00-30.0 min: 10% A to 90% A
30.0-35.0 min: 90% A
35.0-40.0 min: 100% A
Neutral HPLC:
Column: Phenomenex, Jupiter, C4 5 μm 250×10.00 mm, 300 Å
Flow: 6 ml/min
Buffer A: 5 mM TRIS, 7.5 mM $(NH_4)_2SO_4$, pH=7.3, 20% $CH_3CN$
Buffer B: 60% CH3CN, 40% water
Gradient: 0-5 min: 10% B
5-35 min: 10-60% B
35-39 min: 60% B
39-40 min: 70% B
40-43.5 min: 70% B
Anion exchange chromatography:
Column: RessourceQ, 1 ml
Flow: 6 ml/min
Buffer A: 0.09% $NH_4HCO_3$, 0.25% $NH_4OAc$, 42.5% ethanol pH 8.4
Buffer B: 0.09% $NH_4HCO_3$, 2.5% $NH_4OAc$, 42.5% ethanol pH 8.4
Gradient: 100% A to 100% B during 30 column volumes
Desalting:
Column: HiPrep 26/10
Flow: 10 ml/min, 6 column volumes
Buffer: 10 mM $NH_4HCO_3$ General Procedure for the Solid Phase Synthesis of Acylation Reagents of the General Formula (II):

$$Acy\text{-}AA1_n\text{-}AA2_m\text{-}AA3_p\text{-}Act, \qquad (II):$$

wherein Acy, AA1, AA2, AA3, n, m, and p are as defined above and Act is the leaving group of an active ester, such as N-hydroxysuccinimide (OSu), or 1-hydroxybenzotriazole, and wherein carboxylic acids within the Acy and AA2 moieties of the acyl moiety are protected as tert-butyl esters.

Compounds of the general formula (II) according to the invention can be synthesised on solid support using procedures well known to skilled persons in the art of solid phase peptide synthesis. This procedure comprises attachment of a Fmoc protected amino acid to a polystyrene 2-chlorotritylchloride resin. The attachment can, e.g., be accomplished using the free N-protected amino acid in the presence of a tertiary amine, like triethyl amine or N,N-diisopropylethylamine (see references below). The C-terminal end (which is attached to the resin) of this amino acid is at the end of the synthetic sequence being coupled to the parent insulins of the invention. After attachment of the Fmoc amino acid to the resin, the Fmoc group is deprotected using, e.g., secondary amines, like piperidine or diethyl amine, followed by coupling of another (or the same) Fmoc protected amino acid and deprotection. The synthetic sequence is terminated by coupling of mono-tert-butyl protected fatty (α, ω) diacids, like hexadecanedioic, heptadecanedioic, octadecanedioic or eicosanedioic acid monotert-butyl esters. Cleavage of the compounds from the resin is accomplished using diluted acid like 0.5-5% TFA/DCM (trifluoroacetic acid in dichloromethane), acetic acid (e.g., 10% in DCM, or HOAc/trifluoroethanol/DCM 1:1:8), or hecafluoroisopropanol in DCM (See, e.g., "Organic Synthesis on Solid Phase", F. Z.Dörwald, Wiley-VCH, 2000. ISBN 3-527-29950-5, "Peptides: Chemistry and Biology", N. Sewald & H.-D. Jakubke, Wiley-VCH, 2002, ISBN 3-527-30405-3 or "The Combinatorial Cheemistry Catalog" 1999, Novabiochem AG, and references cited therein). This ensures that tert-butyl esters present in the compounds as carboxylic acid protecting groups are not deprotected. Finally, the C-terminal carboxy group (liberated from the resin) is activated, e.g., as the N-hydroxysuccinimide ester (OSu) and used either directly or after purification as coupling reagent in attachment to parent insulins of the invention.

Alternatively, the acylation reagents of the general formula (II) above can be prepared by solution phase synthesis as described below.

Mono-tert-butyl protected fatty diacids, such as hexadecanedioic, heptadecanedioic, octadecanedioic or eicosanedioic acid mono-tert-butyl esters are activated, e.g., as OSu-esters as described below or as any other activated ester known to those skilled in the art, such as HOBt- or HOAt-esters. This active ester is coupled with one of the amino acids AA1, mono-tert-butyl protected AA2, or AA3 in a suitable solvent such as THF, DMF, NMP (or a solvent mixture) in the presence of a suitable base, such as DIPEA or triethylamine. The intermediate is isolated, e.g., by extractive procedures or by chromatographic procedures. The resulting intermediate is again subjected to activation (as described above) and to coupling with one of the amino acids AA1, mono-tert-butyl protected AA2, or AA3 as described above. This procedure is repeated until the desired protected intermediate Acy-AA1$_n$-AA2$_m$-AA3$_p$-OH is obtained. This is in turn activated to afford the acylation reagents of the general formula (II) Acy-AA1$_n$-AA2$_m$-AA3$_p$-Act.

The acylation reagents prepared by any of the above methods can be (tertbutyl) de-protected after activation as OSu esters. This can be done by TFA treatment of the OSu-activated tert-butyl protected acylation reagent. After acylation of any protease stabilised insulin, the resulting unprotected acylated protease stabilised insulin of the invention is obtained.

If the reagents prepared by any of the above methods are not (tert-butyl) deprotected after activation as OSu esters, acylation of any protease stabilised insulin affords the corresponding tert-butyl protected acylated protease stabilised insulin of the invention. In order to obtain the unprotected acylated protease stabilised insulin of the invention, the protected insulin is to be de-protected. This can be done by TFA treatment to afford the unprotected acylated protease stabilised insulin of the invention.

Acylation of a lysine residue (in the epsilon position) of human insulin or an insulin analogue is performed at alkaline pH (eg. at pH 10, 10.5, 11, 11.5, or 12).

The general procedure (A) is illustrated in the first example.

Example 1

General Procedure (A)

A10C, A14E, B4C, B25H, B29K(N$^\epsilon$Octadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]ethoxy]ethoxy]acetyl]amino]ethoxy]-ethoxy]acetyl]-[CysA10,GluA14,CysB4,HisB25],des-ThrB30-Insulin(human)

A10C, B4C, A14E, B25H,desB30 human insulin (2 g) was dissolved in 100 mM aqueous Na$_2$CO$_3$ (50 mL), NMP (3 mL) was added. pH was adjusted to 11.2 with 1 N NaOH. Octadecanedioyl-gGlu-OEG-OEG-OSu (0.8 g, 1.4 equiv.) dissolved in NMP (6 mL) was added simultaneous with 1N NaOH keeping pH at approx. 11. After 5 minutes, water (40 mL) was added and pH was lowered to 5.5 by addition of 1 N HCl. The precipitate was isolated by centrifugation. The residue was dissolved in acetonitrile (30 mL) and water containing 1% TFA (30 mL) and purified by HPLC in 4 runs:

Column: Phenomenex, Gemini, 5µ, C18, 110 A, 250×30 cm
Flow: 20 ml/min'
Eluents: A: 0,1% TFA in water B: 0,1% TFA in acetonitrile
Gradient:
0-7.5 min: 10% B,
7.5-87.5 min: 10% B to 60% B,
87.5-92.5 min: 60% B
92.5-97.5 min: 60% B to 100% B
97.5-100 min: 100% B
100-103 min: 10% B Pure fractions were pooled and lyophilized. The dry material was dissolved in water (200 mL) and added 0,1 N NaOH to pH=8.1 and lyophilised to afford 1 g of the title insulin derivative.

MALDI-MS: m/z: 6340; calcd: 6341.
LC-MS (electrospray): m/z=1586.04 (M+4)/4 (6340)

Example 2

General Procedure (A)

A10C, A14E, B3C, B25H, B29K(N(eps)Octadecanedioyl-gGlu), desB30 Human Insulin
IUPAC (OpenEye, IUPAC style) name:
N{Epsilon-B29}-[(4S)-4-carboxy-4-(17-carboxyheptadecanoylamino)butanoyl]-[CysA10,GluA14,CysB3,HisB25],des-ThrB30-Insulin(human)
LCMS (electrospray): m/z=1517.0 (M+4)/4 (6064)

Example 3

General Procedure (A)

A10C, A14E, B3C, B25H, B29K(N$^\epsilon$Octadecanedioyl), desB30 human insulin
IUPAC (OpenEye, IUPAC style) name:
N{Epsilon-B29}-17-carboxyheptadecanoyl-[CysA10,CysB3,HisB25],des-ThrB30-Insulin(human)
MS (electrospray) m/4: m/z=1485.0 (5935.9). Calcd.: 1484.8

Example 4

General Procedure (A)

A10C, A14E, B3C, B25H, B29K(N$^\epsilon$Octadecanedioyl-gGlu), desB30 human Insulin
IUPAC (OpenEye, IUPAC style) name:
N{Epsilon-B29}-[(4S)-4-carboxy-4-(17-carboxyheptadecanoylamino)butanoyl]-[CysA10,CysB3,HisB25],des-ThrB30-Insulin(Human)
MS (electrospray) m/4: m/z=1525.8 (6099.1). Calcd.: 1525.8

Example 5

General procedure (A)

A10C, A14E, desB1, B4C, B25H, B29K (N$^\epsilon$Octadecanedioyl-gGlu-2xOEG), desB30 Human Insulin
IUPAC (OpenEye, IUPAC style) name:

N{Epsilon-B29}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[CysA10,GluA14,CysB4,HisB25],des-PheB1,ThrB30-Insulin(human)-(A)-peptide,(B2-B29)-peptide MS (electrospray) m/4: m/z=1549.4 (6193.6). Calcd.: 1549.3

The following derivative may be prepared similarly:

Example 6

General Procedure (A)

A10C, A14H, B4C, B25H, B29K(N^εOctadecanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[CysA10,HisA14,CysB4,HisB25],des-ThrB30-Insulin(human)

The following analogues were prepared similarly:

Example 7

General Procedure (A)

A10C, A14E, B3C, B25H, B29K(N^εEicosanedioyl-gGlu-2xOEG), desB30 human insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[CysA10,GluA14,CysB3,HisB25],des-ThrB30-Insulin(human)

MS (electrospray) m/4: m/z=1597.6 (6386.4). Calcd.: 1597.5

Example 8

General Procedure (A)

A10C, A14E, B1C, B25H, B29K(N^εEicosanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[CysA10,GluA14,CysB1,HisB25],des-ThrB30-Insulin(human)

MS (electrospray) m/4: m/z=1588.9 (6351.6). Calcd.: 1588.8

Example 9

General Procedure (A)

A10C, A14E, B4C, B25H, B29K(N^εOctadecanedioyl-gGlu), desB30 human insulin
IUPAC (OpenEye, IUPAC style) name:
N{Epsilon-B29}-[(4S)-4-carboxy-4-(17-carboxyheptadecanoylamino)butanoyl]-[CysA10,GluA14,CysB4,HisB25],des-ThrB30-Insulin(human)

MS (electrospray) m/4: m/z=1514.1 (6351.6). Calcd.: 1513.8

Example 10

General Procedure (A)

A10C, A14E, B3C, B25H, B29K(N^εOctadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]ethoxy]ethoxy]-acetyl]amino]ethoxy]ethoxy]acetyl]-[CysA10,GluA14,CysB3,HisB25],des-ThrB30-Insulin(human)

MS (electrospray) m/4: m/z=1589.6 (6355.4). Calcd.: 1589.9

Example 11

General Procedure (A)

A10C, A14E, B3C, B25H, B29K(N^εOctadecanedioyl-gGlu-gGlu), desB30 human insulin
IUPAC (OpenEye, IUPAC style) name:
N{Epsilon-B29}-[(4S)-4-carboxy-4-[[(4S)-4-carboxy-4-(17-carboxyheptadecanoylamino)butanoyl]amino]butanoyl]-[CysA10,GluA14,CysB3,HisB25],des-ThrB30-Insulin(human)

MS (electrospray) m/4: m/z=1549.2 (6194.2). Calcd.: 1549.6

Example 12

General Procedure (A)

A10C, A14E, B4C, B25H, desB27, B29K(N^εOctadecanedioyl-gGlu), desB30 Human Insulin
IUPAC (OpenEye, IUPAC style) name:
N{Epsilon-B29}-[(4S)-4-carboxy-4-(17-carboxyheptadecanoylamino)butanoyl]-[CysA10,GluA14,CysB4,HisB25],des-ThrB27,ThrB30-Insulin(human)

MS (electrospray) m/4: m/z=1488 (5948). Calcd.: 1488

Example 13

General Procedure (A)

A10C, A14E, B4C, B25H, B29K(N^εOctadecanedioyl), desB30 Human Insulin
IUPAC (OpenEye, IUPAC style) name:
N{Epsilon-B29}-17-carboxyheptadecanoyl-[CysA10,GluA14,CysB4,HisB25],des-ThrB30-Insulin(human)

MS (electrospray) m/4: m/z=1481.9 (5921.9). Calcd.: 1481.5

Example 14

General Procedure (A)

A10C, A14E, B4C, B25H, B29K(N^εOctadecanedioyl-gGlu-gGlu), desB30 Human Insulin
IUPAC (OpenEye, IUPAC style) name:
N{Epsilon-B29}-[(4S)-4-carboxy-4-[[(4S)-4-carboxy-4-(17-carboxyheptadecanoylamino)butanoyl]amino]butanoyl]-[CysA10,GluA14,CysB4,HisB25],des-ThrB30-Insulin(human)

MS (electrospray) m/4: m/z=1546.1 (6180.2). Calcd.: 1545

Example 15

General Procedure (A)

A10C, A14E, B2C, B25H, B29K(N^εOctadecanedioyl-gGlu-OEG-OEG), desB30 Human Insulin IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[CysA10,GluA14,CysB2,HisB25],des-ThrB30-Insulin(human)

MS (electrospray) m/4: m/z=1593.6 (6370.4). Calcd.: 1593.6

Example 16

General Procedure (A)

A10C, A14E, B1C, B25H, B29K(N$^\epsilon$Octadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]ethoxy]ethoxy]acetyl]amino]ethoxy]-ethoxy]acetyl]-[CysA10,GluA14,CysB1,HisB25],des-ThrB30-Insulin(human)

MS (electrospray) m/4: m/z=1581.5 (6322.1). Calcd.: 1581.5

Example 17

General Procedure (A)

A10C, A14E, B3C, B16H, B25H, B29K(N$^\epsilon$Eicosanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]amino]-ethoxy]ethoxy]acetyl]amino]ethoxy]ethoxy]acetyl]-[CysA10,GluA14,CysB3,HisB16,HisB25],des-ThrB30-Insulin(human)

MS (electrospray) m/4: m/z=1590.5 (6357.8). Calcd.: 1590.5

Example 18

General Procedure (A)

A10C, A14E, B4C, B25H, B29K(N$^\epsilon$Myristyl), desB30 Human insulin
IUPAC (OpenEye, IUPAC style) name:
N{Epsilon-B29}-tetradecanoyl-[CysA10,GluA14,CysB4,HisB25],des-ThrB30-Insulin(human)

MS (electrospray) m/4: m/z=1460.0 (5835.8). Calcd.: 1460.0

Example 19

General Procedure (A)

A10C, B4C, B29K(N$^\epsilon$Myristyl), desB30 human insulin
IUPAC (OpenEye, IUPAC style) name:
N{Epsilon-B29}-tetradecanoyl-[CysA10,CysB4],des-ThrB30-Insulin(human)

MS (electrospray) m/3: m/z=1961.4 (5881.2). Calcd.: 1961.4

Example 20

General Procedure (A)

A10C, A14E, B3C, B25H, desB27, B29K(N(eps)octadecanedioyl-gGlu), desB30 Human Insulin
IUPAC (OpenEye, IUPAC style) name:
N{Epsilon-B29}-[(4S)-4-carboxy-4-(17-carboxyheptadecanoylamino)butanoyl]-[CysA10,GluA14,CysB3,HisB25],des-ThrB27,ThrB30-Insulin(human)

MS (electrospray) m/4: m/z=1492.2 (5964.0). Calcd.: 1492.0

Example 21

General Procedure (A)

A10C, A14E, B3C, B25H, desB27, B29K(N(eps)octadecanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[CysA10,GluA14,CysB3,HisB25],des-ThrB27,ThrB30-Insulin(human)

MS (electrospray) m/4: m/z=1564.7 (6254.3). Calcd.: 1564.6

Example 22

General Procedure (A)

A10C, A14E, B3C, B25H, B29K(N$^\epsilon$Eicosanedioyl-gGlu), desB30 Human Insulin
IUPAC (OpenEye, IUPAC style) name:
N{Epsilon-B29}-[(4S)-4-carboxy-4-(19-carboxynonadecanoylamino)butanoyl]-[CysA10,GluA14,CysB3,HisB25],des-ThrB30-Insulin(Human)

MS (electrospray) m/4: m/z=1524.4 (6093.1). Calcd.: 1524.3

Example 23

General Procedure (A)

A10C, A14E, B4C, B25H, B29K(N(eps)eicosanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]-amino]ethoxy]ethoxy]acetyl]amino]ethoxy]ethoxy]acetyl]-[CysA10,GluA14,CysB4,HisB25],des-ThrB30-Insulin(human)

MS (electrospray) m/4: m/z=1593.2 (6369.4). Calcd.: 1593.4

Example 24

General Procedure (A)

A10C, A14E, B3C, B25H, desB27, B29K(N(eps)eicosanedioyl-gGlu), desB30 Human Insulin
IUPAC (OpenEye, IUPAC style) name:
N{Epsilon-B29}-[(4S)-4-carboxy-4-(19-carboxynonadecanoylamino)butanoyl]-[CysA10,GluA14,CysB3,HisB25],des-ThrB27,ThrB30-Insulin(human)

MS (electrospray) m/4: m/z=1499.1 (5992.0). Calcd.: 1499.0

Example 25

General Procedure (A)

A10C, A14E, B3C, B25H, desB27, B29K(N(eps)eicosanedioyl-gGlu-2xOEG), desB30 Human Insulin IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]-amino]ethoxy]ethoxy]acetyl]amino]ethoxy]ethoxy]acetyl]-[CysA10,GluA14,CysB3,HisB25],des-ThrB27,ThrB30-Insulin (human)

MS (electrospray) m/4: m/z=1571.8 (6282.3). Calcd.: 1571.6

Similarly, the following insulin derivatives may be prepared:

Example 26

General Procedure (A)

A10C, A14E, B4C, B25H, B29K(N$^\epsilon$Hexadecanedioyl-gGlu), desB30 Human Insulin
IUPAC (OpenEye, IUPAC style) name:
N{Epsilon-B29}-[(4S)-4-carboxy-4-(15-carboxypentadecanoylamino)butanoyl]-[CysA10,GluA14,CysB4,HisB25],des-ThrB30-Insulin(human)

Example 27

General Procedure (A)

A10C, A14E, B4C, B25H, B29K(N$^\epsilon$Hexadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]ethoxy]ethoxy]acetyl]amino]-ethoxy]ethoxy]acetyl]-[CysA10,GluA14,CysB4,HisB25],des-ThrB30-Insulin(human)

Example 28

General Procedure (A)

A10C, A14E, B4C, B25H, B29K(N$^\epsilon$Hexadecanedioyl), desB30 Human Insulin
IUPAC (OpenEye, IUPAC style) name:
N{Epsilon-B29}-15-carboxypentadecanoyl-[CysA10,GluA14,CysB4,HisB25],des-ThrB30-Insulin(human)

Example 29

General Procedure (A)

A10C, A14E, B4C, B25H, B29K(N$^\epsilon$Hexadecanedioyl-gGlu-gGlu), desB30 human insulin
IUPAC (OpenEye, IUPAC style) name:
N{Epsilon-B29}-[(4S)-4-carboxy-4-[[(4S)-4-carboxy-4-(15-carboxypentadecanoylamino)butanoyl]amino]butanoyl]-[CysA10,GluA14,CysB4,HisB25],des-ThrB30-Insulin(human)

Example 30

General Procedure (A)

A10C, A14E, B4C, B25H, desB27, B29K (N$^\epsilon$Octadecanedioyl-gGlu-OEG-OEG), desB30 Human insulinIUPAC (OpenEye, IUPAC Style) Name:
N{Epsilon-B29}-[2-[2-[2-[[2-[2-[2-[[(4S)-4-carboxy-4-(17-carboxyheptadecanoylamino)butanoyl]amino]ethoxy]acetyl]amino]ethoxy]-ethoxy]acetyl]-[CysA10,GluA14,CysB4,His B25],des-ThrB27,ThrB30-Insulin (human)

Example 31

General Procedure (A)

A10C, A14E, B4C, B25H, desB27, B29K (N$^\epsilon$Octadecanedioyl-gGlu-gGlu), desB30 Human Insulin
IUPAC (OpenEye, IUPAC style) name:
N{Epsilon-B29}-[(4S)-4-carboxy-4-[[(4S)-4-carboxy-4-(15-carboxypentadecanoylamino)butanoyl]amino]butanoyl]-[CysA10,GluA14,CysB4,HisB25],des-ThrB27,ThrB30-Insulin(human)

Example 32

General Procedure (A)

A10C, A14E, B4C, B25H, desB27, B29K (N$^\epsilon$Hexadecanedioyl-gGlu-OEG-OEG), desB30 human insulinIUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]ethoxy]ethoxy]acetyl]amino]ethoxy]-ethoxy]acetyl]-[CysA10,GluA14,CysB4,HisB25],des-ThrB27,ThrB30-Insulin (human)

Example 33

General Procedure (A)

A10C, A14E, B4C, B25H, desB27, B29K(WHexadecanedioyl-gGlu), desB30 Human Insulin
IUPAC (OpenEye, IUPAC style) name:
N{Epsilon-B29}-[(4S)-4-carboxy-4-(15-carboxypentadecanoylamino)butanoyl]-[CysA10,GluA14,CysB4,HisB25],des-ThrB27,ThrB30-Insulin(human)

Example 34

General Procedure (A)

A10C, A14E, B3C, B25H, B29K(N$^\epsilon$Hexadecanedioyl-gGlu), desB30 Human Insulin
IUPAC (OpenEye, IUPAC style) name:
N{Epsilon-B29}-[(4S)-4-carboxy-4-(15-carboxypentadecanoylamino)butanoyl]-[CysA10,GluA14,CysB3,HisB25],des-ThrB30-Insulin(Human)

Example 35

General Procedure (A)

A10C, A14E, B3C, B25H, B29K(N$^\epsilon$Hexadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]-amino]ethoxy]ethoxy]acetyl]amino]ethoxy]ethoxy]acetyl]-[CysA10,GluA14,CysB3,HisB25],des-ThrB30-Insulin(human)

Example 36

General Procedure (A)

A10C, A14E, B2C, B25H, B29K(N$^\epsilon$Hexadecanedioyl-gGlu-OEG-OEG), desB30 human insulin IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[CysA10,GluA14,CysB2,HisB25],des-ThrB30-Insulin(human)

Example 37

General Procedure (A)

A10C, A14E, B2C, B25H, B29K(N$^\epsilon$Hexadecanedioyl-gGlu), desB30 Human Insulin
IUPAC (OpenEye, IUPAC style) name:
N{Epsilon-B29}-[(4S)-4-carboxy-4-(15-carboxypentadecanoylamino)butanoyl]-[CysA10,GluA14,CysB2,HisB25],des-ThrB30-Insulin(human)

Example 38

General Procedure (A)

A10C, A14E, B2C, B25H, B29K(N$^\epsilon$Octadecanedioyl-gGlu), desB30 Human Insulin
IUPAC (OpenEye, IUPAC style) name:
N{Epsilon-B29}-[(4S)-4-carboxy-4-(17-carboxyheptadecanoylamino)butanoyl]-[CysA10,GluA14,CysB2,HisB25],des-ThrB30-Insulin(Human)

Example 39

General Procedure (A)

A10C, A14E, B1C, B25H, B29K(N$^\epsilon$Octadecanedioyl-gGlu), desB30 Human Insulin
IUPAC (OpenEye, IUPAC style) name:
N{Epsilon-B29}-[(4S)-4-carboxy-4-(17-carboxyheptadecanoylamino)butanoyl]-[CysA10,GluA14,CysB1,HisB25],des-ThrB30-Insulin(human)

Example 40

General Procedure (A)

A10C, A14E, B1C, B25H, B29K(N$^\epsilon$Hexadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]-amino]dethoxy]ethoxy]acetyl]amino]dethoxy]ethoxy]acetyl]-[CysA10,GluA14,CysB1,HisB25],des-ThrB30-Insulin(human)

Example 41

General Procedure (A)

A10C, A14E, B1C, B25H, B29K(N$^6$Hexadecanedioyl-gGlu), desB30 human insulin
IUPAC (OpenEye, IUPAC style) name:
N{Epsilon-B29}-[(4S)-4-carboxy-4-(15-carboxypentadecanoylamino)butanoyl]-[CysA10,GluA14,CysB1,HisB25],des-ThrB30-Insulin(human)

Example 42

General Procedure (A)

A10C, B1C, B29K(N$^\epsilon$Hexadecanedioyl-gGlu-OEG-OEG), desB30 Human Insulin

IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]dethoxy]ethoxy]acetyl]amino]ethoxy]ethoxy]acetyl]-[CysA10,CysB1],des-ThrB30-Insulin(human)

Example 43

General Procedure (A)

A10C, B1C, B29K(N$^\epsilon$Hexadecanedioyl-gGlu), desB30 Human Insulin
IUPAC (OpenEye, IUPAC style) name:
N{Epsilon-B29}-[(4S)-4-carboxy-4-(15-carboxypentadecanoylamino)butanoyl]-[CysA10,CysB1],des-ThrB30-Insulin(human)

Example 44

General Procedure (A)

A10C, B1C, B29K(N$^\epsilon$Octadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]dethoxy]ethoxy]acetyl]amino]ethoxy]ethoxy]acetyl]-[CysA10,CysB1],des-ThrB30-Insulin(human)

Example 45

General Procedure (A)

A10C, B1C, B29K(N$^\epsilon$Octadecanedioyl-gGlu), desB30 human insulin
IUPAC (OpenEye, IUPAC style) name:
N{Epsilon-B29}-[(4S)-4-carboxy-4-(17-carboxyheptadecanoylamino)butanoyl]-[CysA10,CysB1],des-ThrB30-Insulin(human)

Example 46

General Procedure (A)

A10C, B2C, B29K(N$^\epsilon$Octadecanedioyl-gGlu-OEG-OEG), desB30 human insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]dethoxy]ethoxy]acetyl]amino]ethoxy]ethoxy]acetyl]-[CysA10,CysB2],des-ThrB30-Insulin(human)

Example 47

General Procedure (A)

A10C, B2C, B29K(N$^\epsilon$Octadecanedioyl-gGlu), desB30 Human Insulin
IUPAC (OpenEye, IUPAC style) name:
N{Epsilon-B29}-[(4S)-4-carboxy-4-(17-carboxyheptadecanoylamino)butanoyl]-[CysA10,CysB2],des-ThrB30-Insulin(human)

Example 48

General Procedure (A)

A10C, B2C, B29K(N$^\epsilon$Hexadecanedioyl-gGlu-OEG-OEG), desB30 Human Insulin

IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]dethoxy]ethoxy]acetyl]amino]ethoxy]ethoxy]acetyl]-[CysA10,CysB2],des-ThrB30-Insulin(human)

Example 49

General Procedure (A)

A10C, B2C, B29K(N${}^{\epsilon}$Hexadecanedioyl-gGlu), desB30 human insulin
IUPAC (OpenEye, IUPAC style) name:
N{Epsilon-B29}-[(4S)-4-carboxy-4-(15-carboxypentadecanoylamino)butanoyl]-[CysA10,CysB2],des-ThrB30-Insulin(human)

Example 50

General Procedure (A)

A10C, B3C, B29K(N${}^{\epsilon}$Hexadecanedioyl-gGlu), desB30 Human Insulin
IUPAC (OpenEye, IUPAC style) name:
N{Epsilon-B29}-[(4S)-4-carboxy-4-(15-carboxypentadecanoylamino)butanoyl]-[CysA10,CysB3],des-ThrB30-Insulin(human)

Example 51

General Procedure (A)

A10C, B3C, B29K(N${}^{\epsilon}$Hexadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]dethoxy]ethoxy]acetyl]amino]ethoxy]ethoxy]acetyl]-[CysA10,CysB3],des-ThrB30-Insulin(human)

Example 52

General Procedure (A)

A10C, B3C, B29K(N${}^{\epsilon}$Octadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]dethoxy]ethoxy]acetyl]amino]ethoxy]ethoxy]acetyl]-[CysA10,CysB3],des-ThrB30-Insulin(human)

Example 53

General Procedure (A)

A10C, B3C, B29K(N${}^{\epsilon}$Octadecanedioyl-gGlu), desB30 Human Insulin
IUPAC (OpenEye, IUPAC style) name:
N{Epsilon-B29}-[(4S)-4-carboxy-4-(17-carboxyheptadecanoylamino)butanoyl]-[CysA10,CysB3],des-ThrB30-Insulin(human)

Example 54

General Procedure (A)

A10C, B4C, B29K(N${}^{\epsilon}$Octadecanedioyl-gGlu), desB30 human insulin
IUPAC (OpenEye, IUPAC style) name:
N{Epsilon-B29}-[(4S)-4-carboxy-4-(17-carboxyheptadecanoylamino)butanoyl]-[CysA10,CysB4],des-ThrB30-Insulin(human)

Example 55

General Procedure (A)

A10C, B4C, B29K(N${}^{\epsilon}$Octadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]dethoxy]ethoxy]acetyl]amino]ethoxy]ethoxy]acetyl]-[CysA10,CysB4],des-ThrB30-Insulin(human)

Example 56

General Procedure (A)

A10C, B4C, B29K(N${}^{\epsilon}$Hexadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]dethoxy]ethoxy]acetyl]amino]ethoxy]ethoxy]acetyl]-[CysA10,CysB4],des-ThrB30-Insulin(human)

Example 57

General Procedure (A)

A10C, B4C, B29K(N${}^{\epsilon}$Hexadecanedioyl-gGlu), desB30 Human Insulin
IUPAC (OpenEye, IUPAC style) name:
N{Epsilon-B29}-[(4S)-4-carboxy-4-(15-carboxypentadecanoylamino)butanoyl]-[CysA10,CysB4],des-ThrB30-Insulin(human)

Example 58

General Procedure (A)

A10C, A14E, I31C, B16H, B25H, B29K(N${}^{\epsilon}$eicosanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]amino]dethoxy]ethoxy]acetyl]amino]ethoxy]ethoxy]acetyl]-[CysA10,GluA14,CysB1,HisB16,HisB25],des-ThrB30-Insulin(human)

Example 59

General Procedure (A)

A10C, A14E, B1C, B16H, B25H, B29K(N${}^{\epsilon}$eicosanedioyl-gGlu), desB30 Human Insulin

Example 60

General Procedure (A)

A10C, A14E, B1C, B16H, B25H, B29K (N$^\epsilon$Octadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[CysA10,GluA14,CysB1,HisB16,HisB25],des-ThrB30-Insulin(human)

Example 61

General Procedure (A)

A10C, A14E, B1C, B16H, B25H, B29K (N$^\epsilon$Octadecanedioyl-gGlu), desB30 Human Insulin
IUPAC (OpenEye, IUPAC style) name:
N{Epsilon-B29}-[(4S)-4-carboxy-4-(17-carboxyheptadecanoylamino)butanoyl]-[CysA10,GluA14,CysB1,HisB16,HisB25],des-ThrB30-Insulin(human)

Example 62

General Procedure (A)

A10C, A14E, B1C, B16H, B25H, B29K (N$^\epsilon$Hexadecanedioyl-gGlu), desB30 Human Insulin
IUPAC (OpenEye, IUPAC style) name:
N{Epsilon-B29}-[(4S)-4-carboxy-4-(15-carboxypentadecanoylamino)butanoyl]-[CysA10,GluA14,CysB1,HisB16,HisB25],des-ThrB30-Insulin(human)

Example 63

General Procedure (A)

A10C, A14E, 131 C, B16H, B25H, B29K (N$^\epsilon$Hexadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[CysA10,GluA14,CysB1,HisB16,HisB25],des-ThrB30-Insulin(human)

Example 64

General Procedure (A)

A10C, A14E, B2C, B16H, B25H, B29K (N$^\epsilon$Hexadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[CysA10,GluA14,CysB2,HisB16,HisB25],des-ThrB30-Insulin(human)

Example 65

General Procedure (A)

A10C, A14E, B2C, B16H, B25H, B29K (N$^\epsilon$Hexadecanedioyl-gGlu), desB30 Human Insulin
IUPAC (OpenEye, IUPAC style) name:
N{Epsilon-B29}-[(4S)-4-carboxy-4-(15-carboxypentadecanoylamino)butanoyl]-[CysA10,GluA14,CysB2,HisB16,HisB25],des-ThrB30-Insulin(human)

Example 66

General Procedure (A)

A10C, A14E, B2C, B16H, B25H, B29K (N$^\epsilon$Octadecanedioyl-gGlu), desB30 Human Insulin
IUPAC (OpenEye, IUPAC style) name:
N{Epsilon-B29}-[(4S)-4-carboxy-4-(17-carboxyheptadecanoylamino)butanoyl]-[CysA10,GluA14,CysB2,HisB16,HisB25],des-ThrB30-Insulin(human)

Example 67

General Procedure (A)

A10C, A14E, B2C, B16H, B25H, B29K (N$^\epsilon$Octadecanedioyl-gGlu-OEG-OEG), desB30 Human Insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[CysA10,GluA14,CysB2,HisB16,HisB25],des-ThrB30-Insulin(human)

Example 68

General Procedure (A)

A10C, A14E, B2C, B16H, B25H, B29K(N$^\epsilon$Eicosanedioyl-gGlu-OEG-OEG), desB30 human insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]amino]dethoxy]ethoxy]acetyl]amino]ethoxy]ethoxy]acetyl]-[CysA10,GluA14,CysB2,HisB16,HisB25],des-ThrB30-Insulin(human)

Example 69

General Procedure (A)

A10C, A14E, B2C, B16H, B25H, B29K(N$^\epsilon$Eicosanedioyl-gGlu), desB30 Human Insulin
IUPAC (OpenEye, IUPAC style) name:
N{Epsilon-B29}-[(4S)-4-carboxy-4-(19-carboxynonadecanoylamino)butanoyl]-[CysA10,GluA14,CysB2,HisB16,HisB25],des-ThrB30-Insulin(human)

Example 70

General Procedure (A)

A10C, A14E, B3C, B16H, B25H, B29K(N$^\epsilon$Eicosanedioyl-gGlu), desB30 human insulin

Example 71

General Procedure (A)

A10C, A14E, B3C, B16H, B25H, B29K (N$^\epsilon$Octadecanedioyl-gGlu-OEG-OEG), desB30 human insulin IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[CysA10,GluA14,CysB3,HisB16,HisB25],des-ThrB30-Insulin(human)

Example 72

General Procedure (A)

A10C, A14E, B3C, B16H, B25H, B29K (N$^\epsilon$Octadecanedioyl-gGlu), desB30 Human Insulin IUPAC (OpenEye, IUPAC style) name:
N{Epsilon-B29}-[(4S)-4-carboxy-4-(17-carboxyheptadecanoylamino)butanoyl]-[CysA10,GluA14,CysB3,HisB16,HisB25],des-ThrB30-Insulin(human)

Example 73

General Procedure (A)

A10C, A14E, B3C, B16H, B25H, B29K (N$^\epsilon$Hexadecanedioyl-gGlu), desB30 Human Insulin IUPAC (OpenEye, IUPAC style) name:
N{Epsilon-B29}-[(4S)-4-carboxy-4-(15-carboxypentadecanoylamino)butanoyl]-[CysA10,GluA14,CysB3,HisB16,HisB25],des-ThrB30-Insulin(human)

Example 74

General Procedure (A)

A10C, A14E, B3C, B16H, B25H, B29K (N$^\epsilon$Hexadecanedioyl-gGlu-OEG-OEG), desB30 Human Insulin IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]dethoxy]ethoxy]acetyl]amino]ethoxy]ethoxy]acetyl]-[CysA10,GluA14,CysB3,HisB16,HisB25],des-ThrB30-Insulin(human)

Example 75

General Procedure (A)

A10C, A14E, B4C, B16H, B25H, B29K (N$^\epsilon$Hexadecanedioyl-gGlu-OEG-OEG), desB30 Human Insulin IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]amino]dethoxy]ethoxy]acetyl]amino]ethoxy]ethoxy]acetyl]-[CysA10,GluA14,CysB4,HisB16,HisB25],des-ThrB30-Insulin(human)

Example 76

General Procedure (A)

A10C, A14E, B4C, B16H, B25H, B29K (N$^\epsilon$Hexadecanedioyl-gGlu), desB30 Human Insulin IUPAC (OpenEye, IUPAC style) name:
N{Epsilon-B29}-[(4S)-4-carboxy-4-(15-carboxypentadecanoylamino)butanoyl]-[CysA10,GluA1 4,CysB4,HisB16,HisB25],des-ThrB30-Insulin(human)

Example 77

General Procedure (A)

A10C, A14E, B4C, B16H, B25H, B29K (N$^\epsilon$Octadecanedioyl-gGlu), desB30 Human Insulin IUPAC (OpenEye, IUPAC style) name:
N{Epsilon-B29}-[(4S)-4-carboxy-4-(17-carboxyheptadecanoylamino)butanoyl]-[CysA10,GluA14,CysB4,HisB16,HisB25],des-ThrB30-Insulin(human)

Example 78

General Procedure (A)

A10C, A14E, B4C, B16H, B25H, B29K (N$^\epsilon$Octadecanedioyl-gGlu-OEG-OEG), desB30 Human Insulin IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]amino]dethoxy]ethoxy]acetyl]amino]ethoxy]ethoxy]acetyl]-[CysA10,GluA1 4,CysB4,HisB16,HisB25],des-ThrB30-Insulin(human)

Example 79

General Procedure (A)

A10C, A14E, B4C, B16H, B25H, B29K(N$^\epsilon$Eicosanedioyl-gGlu-OEG-OEG), desB30 Human Insulin IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]amino]dethoxy]ethoxy]acetyl]amino]ethoxy]ethoxy]acetyl]-[CysA10,GluA14,CysB4,HisB16,HisB25],des-ThrB30-Insulin(human)

Example 80

General Procedure (A)

A10C, A14E, B4C, B16H, B25H, B29K(N$^\epsilon$Eicosanedioyl-gGlu), desB30 Human Insulin IUPAC (OpenEye, IUPAC style) name:
N{Epsilon-B29}-[(4S)-4-carboxy-4-(19-carboxynonadecanoylamino)butanoyl]-[CysA10,GluA14,CysB4,HisB16,HisB25],des-ThrB30-Insulin(human)

Example 81

General Procedure (A)

A10C, A14E, 131C, B25H, B29K(N(Eps)Eicosanedioyl-gGlu), desB30 Human Insulin

IUPAC (OpenEye, IUPAC style) name:
N{Epsilon-B29}-[(4S)-4-carboxy-4-(19-carboxynonadecanoylamino)butanoyl]-[CysA10,GluA14,CysB1,HisB25],des-ThrB30-Insulin(human)

Example 82

General Procedure (A)

A10C, A14E, B2C, B25H, B29K(N(Eps)Eicosanedioyl-gGlu), desB30 Human Insulin
IUPAC (OpenEye, IUPAC style) name:
N{Epsilon-B29}-[(4S)-4-carboxy-4-(19-carboxynonadecanoylamino)butanoyl]-[CysA10,GluA14,CysB2,HisB25],des-ThrB30-Insulin(human)

Example 83

General Procedure (A)

A10C, A14E, B2C, B25H, B29K(N(eps)eicosanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]-amino]dethoxy]ethoxy]acetyl]amino]dethoxy]ethoxy]acetyl]-[CysA10,GluA14,CysB2,HisB25],des-ThrB30-Insulin(human)

Example 84

General Procedure (A)

A10C, A14E, B4C, B25H, desB27, B29K(N(eps)eicosanedioyl-gGlu), desB30 Human Insulin
IUPAC (OpenEye, IUPAC style) name:
N{Epsilon-B29}-[(4S)-4-carboxy-4-(19-carboxynonadecanoylamino)butanoyl]-[CysA10,GluA14,CysB4,HisB25],des-ThrB27,ThrB30-Insulin(human)

Example 85

General Procedure (A)

A10C, A14E, B4C, B25H, desB27, B29K(N(eps)eicosanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]-amino]dethoxy]ethoxy]acetyl]amino]dethoxy]ethoxy]acetyl]-[CysA10,GluA14,CysB4,HisB25],des-ThrB27,ThrB30-Insulin(human)

Example 86

General Procedure (A)

A10C, A14E, B4C, B25H, B29K(N(Eps)Eicosanedioyl-gGlu), desB30 Human Insulin
IUPAC (OpenEye, IUPAC style) name:
N{Epsilon-B29}-[(4S)-4-carboxy-4-(19-carboxynonadecanoylamino)butanoyl]-[CysA10,GluA14,CysB4,HisB25],des-ThrB30-Insulin(human)

Example 87

General Procedure (A)

A10C, A14E, B3C, B25H, desB27, B29K(N(eps)hexadecanedioyl-gGlu), desB30 Human Insulin IUPAC (OpenEye, IUPAC style) name:
N{Epsilon-B29}-[(4S)-4-carboxy-4-(15-carboxypentadecanoylamino)butanoyl]-[CysA10,GluA14,CysB3,HisB25],des-ThrB27,ThrB30-Insulin(human)

Example 88

General Procedure (A)

A10C, A14E, B3C, B25H, desB27, B29K(N(eps)hexadecanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]-amino]dethoxy]ethoxy]acetyl]amino]dethoxy]ethoxy]acetyl]-[CysA10,GluA14,CysB3,HisB25],des-ThrB27,ThrB30-Insulin(human)

Example 89

General Procedure (A)

A10C, A14E, B3C, desB27, B29K(N(eps)hexadecanedioyl-gGlu), desB30 Human Insulin
IUPAC (OpenEye, IUPAC style) name:
N{Epsilon-B29}-[(4S)-4-carboxy-4-(15-carboxypentadecanoylamino)butanoyl]-[CysA10,GluA14,CysB3],des-ThrB27,ThrB30-Insulin(human)

Example 90

General Procedure (A)

A10C, A14E, B3C, desB27, B29K(N(eps)hexadecanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(15-carboxypentadecanoylamino)butanoyl]-amino]dethoxy]ethoxy]acetyl]amino]dethoxy]ethoxy]acetyl]-[CysA10,GluA14,CysB3],des-ThrB27,ThrB30-Insulin(human)

Example 91

General Procedure (A)

A10C, A14E, B3C, desB27, B29K(N(Eps)Octadecanedioyl-gGlu), desB30 Human Insulin
IUPAC (OpenEye, IUPAC style) name:
N{Epsilon-B29}-[(4S)-4-carboxy-4-(17-carboxyheptadecanoylamino)butanoyl]-[CysA10,GluA14,CysB3],des-ThrB27,ThrB30-Insulin(human)

Example 92

General Procedure (A)

A10C, A14E, B3C, desB27, B29K(N(eps)octadecanedioyl-gGlu-2xOEG), desB30 human insulin
IUPAC (OpenEye, IUPAC style) name:
N{Epsilon-B29}-[2-[2-[2-[[2-[2-[2-[[(4S)-4-carboxy-4-(17-carboxyheptadecanoylamino)butanoyl]-amino]dethoxy]ethoxy]acetyl]amino]dethoxy]ethoxy]acetyl]-[CysA10,GluA14,CysB3],des-ThrB27,ThrB30-Insulin(human)

Example 93

General Procedure (A)

A10C, A14E, B3C, desB27, B29K(N(eps)eicosanedioyl-gGlu), desB30 Human Insulin
IUPAC (OpenEye, IUPAC style) name:
N{Epsilon-B29}-[(4S)-4-carboxy-4-(19-carboxynonadecanoylamino)butanoyl]-[CysA10,GluA14,CysB3],des-ThrB27,ThrB30-Insulin(human)

Example 94

General Procedure (A)

A10C, A14E, B3C, desB27, B29K(N(eps)eicosanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]-amino]ethoxy]ethoxy]acetyl]amino]ethoxy]ethoxy]acetyl]-[CysA10,GluA14,CysB3],des-ThrB27,ThrB30-Insulin(human)

Example 95

General Procedure (A)

A10C, A14E, B3C, B16H, B25H, B29K(N(eps)eicosanedioyl-2xgGlu), desB30 Human Insulin
IUPAC (OpenEye, IUPAC style) name:
N{Epsilon-B29}-[(4S)-4-carboxy-4-[[(4S)-4-carboxy-4-(19-carboxynonadecanoylamino)butanoyl]amino]butanoyl]-[CysA10,GluA14,CysB3,HisB16,HisB25],des-ThrB30-Insulin(human)

Example 96

General Procedure (A)

A10C, A14E, B3C, B16E, B25H, B29K(N(eps)eicosanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]amino]dethoxy]ethoxy]acetyl]amino]ethoxy]-ethoxy]acetyl]-[CysA10,GluA14,CysB3,GluB16,HisB25],des-ThrB30-Insulin(human)

Example 97

General Procedure (A)

A10C, A14E, B4C, B16E, B25H, B29K(N(eps)eicosanedioyl-gGlu-2xOEG), desB30 Human Insulin
IUPAC (OpenEye, IUPAC style) name:
N{Epsilon-B29}-[2-[2-[2-[[2-[2-[2-[[(4S)-4-carboxy-4-(19-carboxynonadecanoylamino)butanoyl]amino]dethoxy]ethoxy]-acetyl]amino]ethoxy]ethoxy]acetyl]-[CysA10,GluA14,CysB4,GluB16,HisB25], des-ThrB30-Insulin(human)

Example 98

General Procedure (A)

A10C, A14E, B3C, B16H, B25H, B29K(N(eps)eicosanedioyl-2xgGlu), desB30 Human Insulin
IUPAC (OpenEye, IUPAC style) name:
N{Epsilon-B29}-[(4S)-4-carboxy-4-[[(4S)-4-carboxy-4-(19-carboxynonadecanoylamino)butanoyl]amino]butanoyl]-[CysA10,GluA14,CysB3,HisB16,HisB25],des-ThrB30-Insulin(human)

Example 99

General Procedure (A)

A10C, A14E, B4C, B16E, B25H, B29K(N(eps)eicosanedioyl-2xgGlu), desB30 Human Insulin
IUPAC (OpenEye, IUPAC style) name:
N{Epsilon-B29}-[(4S)-4-carboxy-4-[[(4S)-4-carboxy-4-(19-carboxynonadecanoylamino)butanoyl]amino]butanoyl]-[CysA10,GluA14,CysB4,GluB16,HisB25],des-ThrB30-Insulin(human)

Example 100

Insulin Receptor Binding

Insulin Receptor Binding Assay (on Solubilised Insulin Receptor)

The affinity of the insulin derivative of the invention for the human insulin receptor was determined by a Scintillation Proximity Assay (SPA) (according to Glendorf et al. (2008), *Biochemistry*, 47, 4743-4751). Competition binding experiments were performed in 96-well plates (polystyrene Optiplate-96, PerkinElmer) on an Eppendorf epMotion 5075 robot using solubilized human IR (holoreceptor) semipurified by wheat germ agglutinin purification from baby hamster kidney (BHK) cells, which were stably transfected with the pZem vector containing the human IR-A or IR-B insert. Assays were initiated by making dilution series (eight dilutions, 5-fold each, first dilution 43-fold) of yeast supernatant containing the insulin derivative and a human insulin standard. A reagent mix consisting of SPA beads (SPA PVT Antibody-Binding Beads, Anti-Mouse Reagent Cat. No. RPNQ0017, GE Healthcare) resuspended in binding buffer, anti-IR monoclonal mouse antibody (83-7), solubilized human IR (hIRA or hIR-B), and [$^{125}$I]A14Tyr-labelled insulin was added to the dilution series of the appropriate samples. The final concentration of [$^{125}$I]A14Tyr-labelled insulin was 7.5 µM, and the buffer consisted of 100 mM HEPES (pH 7.8), 100 mM NaCl, 10 mM MgSO4, and 0.025% (v/v) Tween 20. Plates were incubated with gentle shaking for 24 h at room temperature, centrifuged for 2 minutes at 2000 rpm, and counted in a TopCount NXT for 3 min/well. Data from the SPA were analyzed according to the four-parameter logistic model (Volund, A., (1978), *Biometrics*, 34, 357-365.) and the affinities of the insulin derivative expressed relative to that of human insulin.

This assay is also run with 1.5% HSA in the assay buffer in order to mimic physiological conditions.

Preparation of Monoclonal mIR Antibodies

Specific antibodies (F12 or 83-7) were produced by monoclonal technique: RBF mice were immunized by injecting 50 µg of purified mIR in FCA subcutaneously followed by two injections with 20 µg of mIR in FIA. High responder mice were boosted intravenously with 25 µg of mIR and the spleens were harvested after 3 days. Spleen cells were fused with the myeloma Fox cell line (Köhler, G & Milstein C. (1976), European J. Immunology, 6:511-19; Taggart R T et al (1983), Science 219:1228-30). Supernatants were screened for antibody production in a mIR specific ELISA. Positive wells are cloned and tested in Western blotting.

Insulin Receptor Binding Assay (on Membrane-Associated Insulin Receptor)

Binding of [$^{125}$I]-human insulin to membrane-associated recombinant human insulin receptor isoform A (hIR-A)

Extraction of membrane-associated insulin receptors: BHK cells (tk-ts13) expressing the human insulin receptor isoform A from a ten-layer cell factory were harvested and homogenised in 25 ml of ice-cold buffer (25 mM HEPES pH 7.4, 2.5 mM CaCl$_2$, 1 mM MgCl$_2$, 250 mg/l bacitracin, 0.1 mM Pefablock (Roche)). The homogenate was layered carefully on 41% sucrose cushions, centrifuged in the ultracentrifuge at 95,000×g for 75 minutes in a Beckman SW28 rotor at 4° C. The plasma membranes were collected from the top of the sucrose cushion, diluted 1:4 with buffer and centrifuged at 40,000×g for 45 min in a Beckman SW28 rotor. The pellets were suspended in buffer (25 mM HEPES pH 7.4, 2.5 mM CaCl$_2$, 1 mM MgCl$_2$, 250 mg/l bacitracin, 0.1 mM Pefablock) and stored at −80° C.

Radioligand binding to membrane-associated insulin receptors was performed in duplicate in 96-well Opti Plates (Perkin Elmer). Membrane protein was incubated for 150 minutes at 25° C. with 50 pM [$^{125}$I-Tyr$^{414}$]-human insulin in a total volume of 200 ml assay buffer (50 mM HEPES, 150 mM NaCl, 5 mM MgSO$_4$, 0.01% Triton X-100, 0.1% HSA (fatty acid free), Complete™ EDTA-free protease inhibitors), increasing concentrations of human insulin or insulin derivative (typically between 0.01 and 300 nM), and 1 mg of WGA-coated PVT microspheres (GE Healthcare). The assay was terminated by centrifugation of the plate at 2000 RPM for 2 minutes, and bound radioactivity quantified by counting in a Packard TopCount NXT after a delay of 60 minutes.

The binding data were fitted using the four-parameter sigmoidal regression algorithm in GraphPad Prism 5.02 (GraphPad Software, San Diego, Calif.). Results are given as IC$_{50}$ relative to human insulin in %.

Insulin receptor affinities:

| Example No. | Relative IR-A affinity SPA assay (@ 0% HSA) (%) | Relative IR-A affinity SPA assay (@ 1.5% HSA) (%) |
|---|---|---|
| 1 | 3.38 | 0.39 |
| 2 | 0.64 | 0.23 |
| 10 | 1.90 | 0.15 |
| 3 | 1.13 | 0.01 |
| 11 | 0.44 | 0.06 |
| 12 | 3.68 | 0.39 |
| 13 | 5.14 | 0.52 |
| 14 | 1.90 | 0.25 |
| 4 | 2.79 | 0.18 |
| 9 | 3.98 | 0.89 |
| 15 | 2.57 | 0.04 |
| 16 | 0.60 | 0.03 |
| 17 | 0.17 | 0.01 |
| 18 | | 0.27 |
| 19 | 29.29 | 0.48 |
| 5 | 2.54 | 0.08 |
| 20 | 1.00 | 0.06 |
| 21 | 1.05 | 0.06 |
| 7 | 0.50 | 0.05 |
| 8 | 0.40 | 0.03 |
| 22 | 0.42 | 0.01 |
| 23 | 2.18 | |
| 24 | 0.45 | 0.03 |
| 25 | 0.66 | 0.08 |

The impact of the additional disulfide bridge in the insulin derivatives of the invention is—surprisingly—only minor. The effect of the fatty acid side chain is making the largest impact, second to the impact of the none-cysteine mutations in the parent insulin. This is illustrated in the following table and is a general finding. Low insulin receptor affinity of fatty acid derivatised insulins of the invention is desired in order to obtain long and protracted in vivo profiles.

| Example No. | Side chain | Parent insulin mutations (rel. to HI) | Relative IR-A affinity SPA assay (@ 0% HSA) | Relative IR-A affinity SPA assay (@ 1.5% |
|---|---|---|---|---|
| | | desB30 | 100.0 | |
| | | A14E, B25H, desB30 | 25.0 | |
| | | A10C, B4C, desB30 | 162.4 | |
| | | A10C, B3C, desB30 | 51.3 | |
| | | A10C, B2C, desB30 | 164.9 | |
| | | A10C, B1C, desB30 | 56.9 | |
| | | A10C, A14E, B4C, B25H, | 37.8 | |
| | | A10C, A14E, B3C, B25H, | 11.4 | |
| | | A10C, A14E, B2C, B25H, | 37.1 | |
| | | A10C, A14E, B1C, B25H, | 13.2 | |
| | C18-gGlu- | desB30 | 10.4 | 0.70 |
| | C18-gGlu- | A14E, B25H, desB30 | 2.3 | 0.11 |
| 1 | C18-gGlu- | A10C, A14E, B4C, B25H, | 3.4 | 0.39 |
| 10 | C18-gGlu- | A10C, A14E, B3C, B25H, | 1.9 | 0.15 |
| 15 | C18-gGlu- | A10C, A14E, B2C, B25H, | 2.6 | 0.04 |
| 16 | C18-gGlu- | A10C, A14E, B1C, B25H, | 0.6 | 0.03 |

Example 101

Hydrophobicity of the Insulin Derivatives of the Invention

The hydrophobicity of an insulin derivative is found by reverse phase HPLC run under isocratic conditions. The elution time of the insulin derivative is compared to that of human insulin (herein designated HI) or another derivative with a known hydrophibicity under the same conditions. The hydrophobicity, k' rel, is calculated as: k'rel$_{deriv}$=(($t_{deriv}$−$t_0$)/($t_{ref}$−$t_0$))*k'rel$_{ref}$. Using HI as reference: k'rel$_{ref}$=k'rel$_{HI}$=1. The void time of the HPLC system, $t_0$, is determined by injecting 5 µl of 0.1 mM NaNO$_3$. Runing conditions:

Column: Lichrosorb RP-C18, 5 µm, 4×250 mm

Buffer A: 0.1 M natrium phosphate pH 7.3, 10 vol % CH$_3$CN

Buffer B: 50 vol % CH$_3$CN

Injection volume: 5 µl

Run time: max 60 minutes

After running an initial gradient, the isocratic level for running the derivative and reference (for example HI) is chosen, and the elution times of the derivative and reference under isocratic conditions are used in the above equation to calculate k'rel$_{deriv}$.

Example 102

Degradation of Insulin Derivaitves Using Duodenum Lumen Enzymes

Degradation of insulin derivatives using duodenum lumen enzymes (prepared by filtration of duodenum lumen content) from SPD rats.

The assay was performed by a robot in a 96 well plate (2 ml) with 16 wells available for insulin derivatives and standards. Insulin derivatives ~15 µM were incubated with duodenum enzymes in 100 mM Hepes, pH=7.4 at 37° C., samples were taken after 1, 15, 30, 60, 120 and 240 min and reaction quenched by addition of TFA. Intact insulin derivatives at each point were determined by RP-HPLC. Degradation half time was determined by exponential fitting of the data and normalized to half time determined for the reference insulins, A14E, B25H, desB30 human insulin or human insulin in each assay. The amount of enzymes added for the degradation was such that the half time for degradation of the reference insulin was between 60 min and 180 min. The result is given as the degradation half time for the insulin derivative in rat duodenum divided by the degradation half time of the reference insulin from the same experiment (relative degradation rate).

| Example No. | Duodenum degradation. Relative stability vs. A14E, B25H, desB30 human insulin |
|---|---|
| 1 | 1.9 |
| 2 | 3.2 |
| 10 | 2.1 |
| 3 | 1.2 |
| 11 | 2.3 |
| 12 | 13.4 |
| 13 | 0.9 |
| 14 | 3.6 |
| 4 | 1.5 |
| 9 | 3.1 |
| 15 | 4.3 |
| 16 | 1.5 |
| 17 | 1.4 |
| 18 | 0.4 |
| 19 | 0.1 |
| 5 | 2.9 |
| 6 | |
| 20 | |
| 21 | |
| 7 | 1.7 |
| 8 | 0.6 |
| 22 | 2.8 |
| 23 | 1.2 |
| 24 | |
| 25 | 6.1 |

Example 103

Rat Pharmacokinecics, Intravenous Rat PK

Anaesthetized rats were dosed intravenously (i.v.) with insulin derivatives at various doses and plasma concentrations of the employed compounds were measured using immunoassays or mass spectrometry at specified intervals for 4 hours or more post-dose. Pharmacokinetic parameters were subsequently calculated using WinNonLin Professional (Pharsight Inc., Mountain View, Calif., USA).

Non-fasted male Wistar rats (Taconic) weighing approximately 200 gram were used.

Body weight was measured and rats were subsequently anaesthetized with Hypnorm/Dormicum (each compound is separately diluted 1:1 in sterile water and then mixed; prepared freshly on the experimental day). Aanaesthesia was initiated by 2 ml/kg Hypnorm/Doricum mixture sc followed by two maintenance doses of 1 ml/kg sc at 30 min intervals and two maintenance doses of 1 ml/kg sc with 45 min intervals. If required in order to keep the rats lightly anaesthetised throughout a further dose(s) 1-2 ml/kg sc was supplied. Weighing and initial anaesthesia was performed in the rat holding room in order to avoid stressing the animals by moving them from one room to another.

PK profiles are shown in FIG. 1

Example 104

Dog Pharmacokinecics, Intravenous Dog PK

Male Beagle dogs (approximately 12 kg) receives a single dose intravenously of insulin insulin analogue (2 nmol/kg). Blood is drawn and plasma collected at time points −0.17, 0, 0.083, 0.25, 0.5, 0.75, 1, 1.25, 1.5, 2, 2.5, 3, 3.5, 4, 5, 8, 10, 12, 16, 24, 32, 48, 72, 96, 120, 144 and 168 hours after dosing. Plasma samples are analyzed by either sandwich immunoassay or LCMS. Plasma concentration-time profiles are analysed by non-compartmental pharmacokinetics analysis using WinNonlin Professional 5.2 (Pharsight Inc., Mountain View, Calif., USA).

Example 105

Rat Pharmacokinecics, Rat PK Following Intraintestinal Injection

Anaesthetized rats are dosed intraintestinally (into jejunum) with insulin derivatives. Plasma concentrations of the employed compounds as well as changes in blood glucose are measured at specified intervals for 4 hours or more post-dosing. Pharmacokinetic parameters are subsequently calculated using WinNonLin Professional (Pharsight Inc., Mountain View, Calif., USA).

Male Sprague-Dawley rats (Taconic), weighing 250-300 g, fasted for ~18 h are anesthetized using Hypnorm-Dormicum s.c. (0.079 mg/ml fentanyl citrate, 2.5 mg/ml fluanisone and 1.25 mg/ml midazolam) 2 ml/kg as a priming dose (to timepoint −60 min prior to test substance dosing), 1 ml/kg after 20 min followed by 1 ml/kg every 40 min.

The insulins to be tested in the intraintestinal injection model are formulated according to the following composition (in weight %):

| | |
|---|---|
| 45% Propylene glycol | (Merck) |
| 33% Capmul MCM C10 | (Abitec) |
| 11% Poloxamer 407 | (BASF) |
| 11% Polyethyleneglycol 3350 Ultra | (Fluka) |

The amount of added insulin is subtracted equally from Capmul MCM C10, Poloxamer 407 and PEG 3350 and not from propylene glycol in order to keep the amount of propylene glycol independent of the drug load constant at 45%.

The anesthetized rat is placed on a homeothermic blanket stabilized at 37° C. A 20 cm polyethylene catheter mounted a 1-ml syringe is filled with insulin formulation or vehicle. A 4-5 cm midline incision is made in the abdominal wall. The catheter is gently inserted into mid-jejunum ~50 cm from the caecum by penetration of the intestinal wall. If intestinal content is present, the application site is moved ±10 cm. The catheter tip is placed approx. 2 cm inside the lumen of the intestinal segment and fixed without the use of ligatures. The intestines are carefully replaced in the abdominal cavity and the abdominal wall and skin are closed with autoclips in each layer. At time 0, the rats are dosed via the catheter, 0.4 ml/kg of test compound or vehicle.

Blood samples for the determination of whole blood glucose concentrations are collected in heparinised 10 µl capillary tubes by puncture of the capillary vessels in the tail tip. Blood glucose concentrations are measured after dilution in 500 µl analysis buffer by the glucose oxidase method using a Biosen autoanalyzer (EKF Diagnostic Gmbh, Germany). Mean blood glucose concentration courses (mean±SEM) are made for each compound.

Samples are collected for determination of the plasma insulin concentration. 100 µl blood samples are drawn into chilled tubes containing EDTA. The samples are kept on ice until centrifuged (7000 rpm, 4° C., 5 min), plasma is pipetted into Micronic tubes and then frozen at 20° C. until assay. Plasma concentrations of the insulin derivatives are measured in a immunoassay which is considered appropriate or validated for the individual derivative.

Blood samples are drawn at t=−10 (for blood glucose only), at t=−1 (just before dosing) and at specified intervals for 4 hours or more post-dosing.

Example 106

Potency of the Acylated Insulin Derivatives of this Invention Relative to Human Insulin, Intravenous Steady-State Clamp Sprague Dawley male rats weighing 238-383 g on the experimental day are used for the clamp experiment. The rats have free access to feed under controlled ambient conditions and are fasted overnight (from 3 pm) prior to the clamp experiment.
Experimental Protocol:

The rats are acclimatized in the animal facilities for at least 1 week prior to the surgical procedure. Approximately 1 week prior to the clamp experiment, Tygon catheters are inserted under halothane anaesthesia into the jugular vein (for infusion) and the carotid artery (for blood sampling) and exteriorised and fixed on the back of the neck. The rats are given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) is administered during anaesthesia and Rimadyl (1.5 mg/kg, s.c.) is administered after full recovery from the anaesthesia (2-3 h) and again once daily for 2 days.

At 7 am on the experimental day overnight fasted (from 3 pm the previous day) rats are weighed and connected to the sampling syringes and infusion system (Harvard 22 Basic pumps, Harvard, and Perfectum Hypodermic glass syringe, Aldrich) and then placed into individual clamp cages where they rest for ca. 45 min before start of experiment. The rats are able to move freely on their usual bedding during the entire experiment and have free access to drinking water. After a 30 min basal period during which plasma glucose levels were measured at 10 min intervals, the insulin derivative to be tested and human insulin (one dose level per rat, n=6-7 per dose level) are infused (i.v.) at a constant rate for 300 min. Optionally a priming bolus infusion of the insulin derivative to be tested is administered in order to reach immediate steady state levels in plasma. The dose of the priming bolus infusion can be calculated based on clearance data obtained from i.v. bolus pharmacokinetics by a pharmacokinetician skilled in the art. Plasma glucose levels are measured at 10 min intervals throughout and infusion of 20% aqueous glucose is adjusted accordingly in order to maintain euglyceamia. Samples of re-suspended erythrocytes are pooled from each rat and returned in about ½ ml volumes via the carotid catheter.

On each experimental day, samples of the solutions of the individual insulin derivatives to be tested and the human insulin solution are taken before and at the end of the clamp experiments and the concentrations of the peptides are confirmed by HPLC. Plasma concentrations of rat insulin and C-peptide as well as of the insulin derivative to be tested and human insulin are measured at relevant time points before and at the end of the studies. Rats are killed at the end of experiment using a pentobarbital overdose.

Example 107

Potency of the Acylated Insulin Derivatives of this Invention Relative to a Control Insulin Derivative, Subcutaneous Administration to Rats Male Sprague-Dawley rats (n=6 per group) receives a single dose subcutaneously of vehicle or insulin insulin analogue (50 or 200 nmol/animal for analogues with a medium duration of action or long duration of action, recpectively). Blood (sublingual) is drawn and plasma collected at time points 0, 1, 2, 4, 8, 24 and 48 or 0, 2, 4, 8, 24, 48, 72, 96 hours after dosing, for analogues with a medium duration of action or long duration of action, receptively). Plasma is assayed for glucose. The glucose lowering effect is calculated as the area under the curve of -delta plasma glucose as a function of time and compared to a control insulin derivative.

Example 108

Melting Temperature Determinations

Differential Scanning Calorimetry (DSC).

Data collection was performed using a VP-DSC differential scanning micro-calorimeter (MicroCal, LLC, Northampton, Mass.). All protein scans (~200 µM insulin derivatives) were performed with 2 mM phosphate buffer in the reference cell from 15° C. to 120° C. at a scan rate of 1° C./min and an excess pressure of 0.21 MPa. All samples and references were degassed immediately before use. A buffer-buffer reference scan was subtracted from each sample scan prior to concentration normalization.

Figure 3:
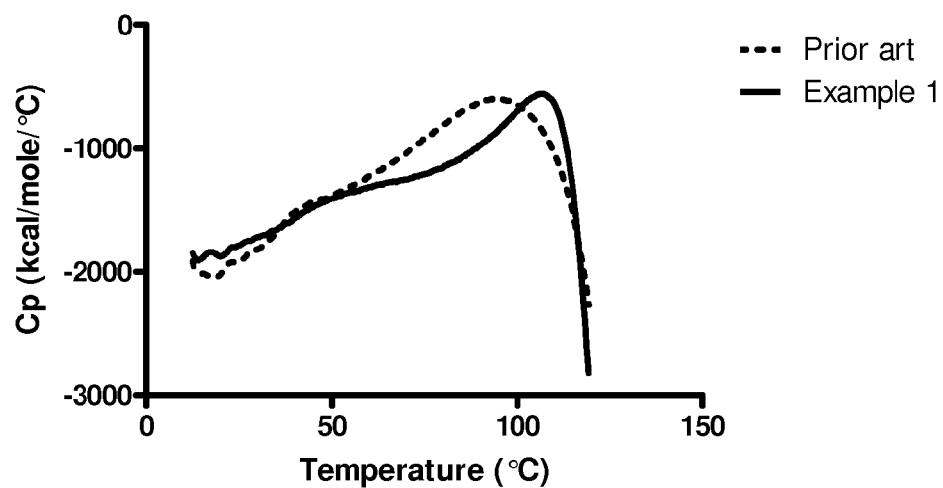
FIG. 3: Differential Scanning calorimetry (DSC) data of insulin derivatives of the invention.
Figure 4:
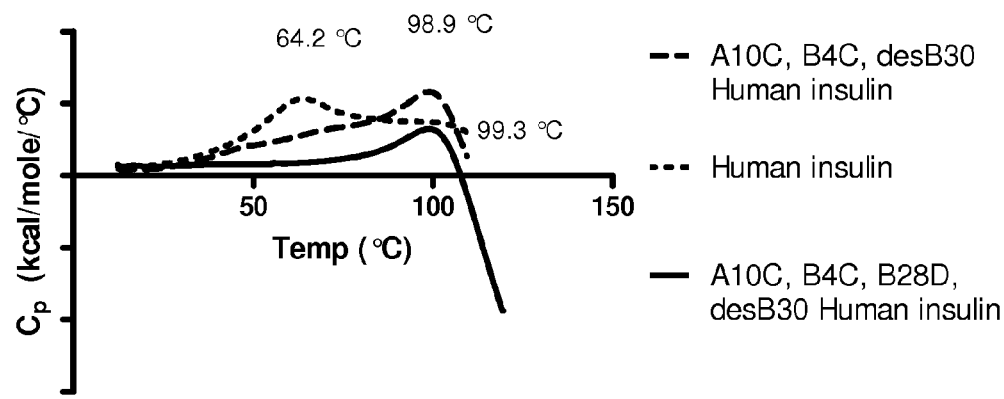
FIG. 4: Differential Scanning calorimetry (DSC) data of parent insulin analogues.

DSC data are shown in FIGS. 3 and 4

Example 109

Measurement of Tendencies of Fibrillation

General Procedure for Thioflavin T (ThT) Fibrillation Assay:
Principle

Low physical stability of a peptide may lead to amyloid fibril formation, shich is observed as well-ordered, thread-like macromolecular structures in the sample eventually resulting in gel formation. This has traditionally been measured by visual inspection of the sample. However, that kind of measurement is very subjective and depending on the observer. Therefore the application of a small molecule indicator probe is much preferred. Thioflavin T (ThT) is such a probe and has a distinct fluorescence signature when binding to fibrils (Naiki et al. Anal. Biochem. 177, 244-249, 1989; Le-Vine, Methods Enzymol. 309, 274-284, 1999). The time course for fibril formation can be described by a sigmoidal curve with the following expression (Nielsen at al. Biochemistry 40, 6036-6046, 2001):

$$F = f_i + m_i t + \frac{f_f + m_f t}{1 + e^{-[(t-t_0)/\tau]}}$$   Eq. (1)

Here, F is the ThT fluorescence at the time t. The constant $t_0$ is the time needed to reach 50% of maximum fluorescence. The two important parameters describing fibril formation are the lag-time calculated by $t_0 - 2\tau$ and the apparent rate constant $k_{app} = 1/\tau$.

Formation of a partially folded intermediate of the peptide is suggested as a general initiating mechanism for fibrillation. Few of those intermediates nucleate to form a template onto which further intermediates may assemle and the fibrillation proceeds. The lag-time corresponds to the interval in which the critical mass of nucleus is built up and the apparent rate constant is the rate with which the fibril itself is formed.

Sample Preparation

Samples were prepared freshly before each assay. Each analog was dissolved in 7 mM sodium phosphate, pH=7.4. Thioflavin T was added to the samples from a stock solution in water to a final concentration of 1 μM. Sample aliquots of 200 μl were placed in a 96 well microtiter plate (Packard Optiplate™-96, white polystyrene). Usually four replica of each sample (corresponding to one test condition) were placed in one column of wells. The plate was sealed with Scotch Pad (Qiagen).

Incubation and Fluorescence Measurements

Incubation at given temperature, shaking and measurements of the ThT fluorescence emission were done in either a Fluoroskan Ascent FL or Varioskan fluorescence plate reader (thermo Labsystems). The temperature was adjusted to 37° C. The orbital shaking was adjusted to 960 rpm with an amplitude of 1 mm in all the presented data. Fluorescence measurements were done using excitation through a 444 nm filter and measurement of emission through a 485 nm filter.

Each run was initiated by incubating the plate at the assay temperature for 10 min. The plate was measured every 20 minutes for typically 45 hours. Between each measurement, the plate was shaken and heated as described above.

Data Handling

The measurement data points were saved in Microsoft Excel format for further processing and curve drawing and fitting was performed using Graph Pad Prism. The background emission from ThT in the absence of fibrils was negligible. The data points are typically a mean of four samples. Only data obtained in the same experiment (i.e. samples on the same plate) are presented in the same graph ensuring a relative measure of fibrillation between the individual samples of one assay rather then comparison between different assays.

The data set may be fitted to Eq. (1). However since the full sigmoidal curves are not usually achieved during the measurement time, the degree of fibrillation is expressed as ThT fluorescence at various time points calculated as the mean of the four samples and shown with the standard deviation

|  | 0 h | 2 h | 20 h | 45 h |
|---|---|---|---|---|
| Human insulin | 28 ± 1 | 1567 ± 46 | 1780 ± 40 | 1732 ± 48 |
| A10C, A14E, B4C, B25H, B29K(N$^\varepsilon$Octadecanedioyl-gGlu-OEG-OEG), desB30 human insulin (Example 1) | 33 ± 1 | 24 ± 1 | 24 ± 1 | 24 ± 2 |
| A10C, A14E, B3C, B25H, B29K(N(eps)Octadecanedioyl-gGlu), desB30 human insulin (Example 2) | 36 ± 1 | 29 ± 0 | 28 ± 0 | 31 ± 0 |

| Example No. | ThT 0 h | ThT 2 h | ThT 20 h | ThT 45 h |
|---|---|---|---|---|
| 1 | 33.3 + 1.4 | 23.6 + 1.1 | 23.8 + 0.7 | 23.5 + 1.6 |
| 2 | 35.8 + 0.7 | 28.7 + 0.4 | 28.4 + 0.2 | 31.3 + 0.2 |
| 3 | 34.4 ± 0.9 | 24.3 ± 0.8 | 23 ± 1.3 | 21.9 ± 0.8 |
| 11 | 23.2 ± 0.7 | 14.3 ± 0.6 | 14.2 ± 1.9 | 14.5 ± 2 |
| 12 | 28.4 ± 0.1 | 20.1 ± 1.5 | 19.8 ± 3.5 | 19.9 ± 3.8 |
| 13 | 55.9 ± 1.2 | 31 ± 0.1 | 29.9 ± 0.5 | 28.1 ± 0.6 |
| 14 | 22.2 ± 0.5 | 15.5 ± 0.3 | 16.2 ± 0.2 | 16.6 ± 0.2 |
| 4 | 31 ± 0.5 | 24.9 ± 0.3 | 25.9 ± 0.3 | 24.9 ± 0.1 |
| 9 | 25.8 ± 0.9 | 17.1 ± 0.2 | 17 ± 0.3 | 16.8 ± 0.3 |
| 15 | 27.7 ± 0.3 | 20.7 ± 0.3 | 20 ± 0.5 | 19.3 ± 0.4 |
| 16 | 25 ± 0.4 | 17.2 ± 0.4 | 18.2 ± 0.3 | 18.6 ± 0.3 |
| 17 | 27.5 ± 0.6 | 17.7 ± 0.7 | 17.5 ± 1.3 | 16.9 ± 1.3 |
| 18 | 63.7 ± 0.8 | 38.6 ± 3 | 34.7 ± 5.4 | 31.9 ± 5.3 |
| 19 | 63.3 ± 1.8 | 41.5 ± 1.4 | 35.9 ± 1.9 | 30.7 ± 1.8 |
| 5 | 27.5 ± 0.3 | 16.3 ± 0.9 | 14.8 ± 2.4 | 14.3 ± 2.7 |
| 21 | 25.9 ± 0.1 | 14.7 ± 0.4 | 16.1 ± 0.7 | 15.8 ± 0.7 |

It is evident that none of the insulins according to the invention that were tested towards fibrillation in the ThT assay showed any signs of fibrillation as seen by (absence of) increased fluorescence as a function of time. This is very unusual and this understates the utility of the analogues of the invention.

Example 110

Lipogenesis in Rat Adipocytes

As a measure of in vitro potency of the insulins of the invention, lipogenesis can be used.

Primary rat adipocytes are isolated from the epididymale fat pads and incubated with 3H-glucose in buffer containing e.g. 1% fat free HSA and either standard (human insulin, HI) or insulin of the invention. The labelled glucose is converted into extractable lipids in a dose dependent way, resulting in full dose response curves. The result is expressed as relative potency (%) with 95% confidence limits of insulin of the invention compared to standard (HI).

Lipogenesis data for insulins of the invention:

| Example No | Lipogenesis in presence of 0.1% HSA, relative potency compared to human insulin (%) |
|---|---|
| 1 without disulfide bond (prior art) | 0.31 |
| 18 | 3.24 |
| 19 | 1.69 |
| 1 | 0.45 |
| 2 | 0.24 |
| 3 | 0.04 |
| 11 | 0.08 |
| 12 | 0.40 |
| 13 | 0.57 |
| 14 | 0.19 |
| 4 | 0.14 |
| 9 | 0.98 |
| 15 | 0.13 |
| 16 | 0.08 |
| 5 | 0.24 |
| 17 | 0.02 |
| 7 | 0.04 |
| 8 | 0.05 |
| 24 | 0.03 |
| 25 | 0.04 |

For the majority of the analogues according to the invention there is a very good accordance between the obtained lipogenesis data (in presence of 0.1% HSA) and the insulin receptor data obtained in presence of 1.5% HSA, thus confirming that the receptor binding is translated into receptor activation.

Example 111

Chemical Stability of the Insulin Analogues of the Invention

Chemical stability of an insulin analogue is assessed after incubating insulin analogue in 2 mM phosphate, pH=7.5 at 37° C. for up to 8 weeks. Formation of high molecular weight products (HMWP) is determined by SEC HPLC analysis after 0, 2, 4 and optionally 8 weeks. The results of the SEC method are given as a difference between HMWP formation at 37° C. and 5° C. start sample as a percentage of total absorbance at 215 nm. Chemical degradation products are determined by RP HPLC analysis after 0, 2, 4 and optionally 8 weeks. The results of the RP method are given as a difference between chemical degradation observed at 37° C. and 5° C. start sample as a percentage of total absorbance at 215 nm.

SEC-HPLC Method:
Solvent: 500 mM NaCl, 10 mM $NaH_2PO_4$, 5 mM $H_3PO_4$, 50% (v/v) 2-propanol
Flow: 0.5 ml/min
Run time: 30 min
UV Detection: 215 nm
Column: Insulin HMWP column from Waters 7.8×300 mm
Temperature: 50° C.
RP-HPLC Method:
Solvent A: 0.09M phosphate buffer pH 3.6 (diammoniumhydrogenphosphate),10% MeCN (v/v)
Solvent B: 80% MeCN (v/v %)
Flow: 0.3 ml/min
Runtime: 33 min
UV Detection: 215 nm
Column: Waters Acquity BEH130 C18 Column 1.7 pm, 150×2.1 mm
Temperature: 50° C.

Gradient:

| Time, min | Flow, ml/min | % A | % B |
|---|---|---|---|
| 0 | 0.3 | 95 | 5 |
| 2 | 0.3 | 95 | 5 |
| 25 | 0.3 | 45 | 55 |
| 27 | 0.3 | 20 | 80 |
| 28 | 0.3 | 20 | 80 |
| 29 | 0.3 | 95 | 5 |
| 33 | 0.3 | 95 | 5 |

| Example No. | Chemical degradation (%) (4 weeks 37° C. - 0 weeks 5° C.) | HMWP Formation (%) (4 weeks 37° C. - 0 weeks 5° C.) |
|---|---|---|
| 1 without A10-B4 disulfide bridge (prior art) | 11.7 | 1.0 |
| 18 | 4.2 | 5.1 |
| 19 | 11.7 | 34.6 |
| 1 | 6.8 | 0.9 |
| 2 | 2.5 | 0.0 |
| 3 | 3.4 | 0.7 |
| 11 | 3.2 | −0.2 |
| 12 | 7.3 | −0.1 |
| 13 | 9.8 | 0.5 |
| 14 | 9.7 | 0.0 |
| 4 | 8.7 | −0.4 |
| 9 | 5.7 | 0.7 |
| 15 | 10.4 | 1.2 |
| 16 | 58.0 | 42.7 |
| 5 | 12.5 | 0.4 |
| 17 | 13.3 | 0.2 |
| 7 | 0.6 | 0.4 |
| 8 | 66.4 | 54.5 |
| 24 | 2.0 | 0.4 |
| 25 | 1.9 | 0.8 |

It is concluded that analogues with a disulfide to B3 are in general more stable than analogues with a disulfide to B4, and analogues with disulfide to B2 or B1 are less stable.

Example 112

X-Ray Structure Determination

An example of crystallization conditions is given bellow, however, the exact conditions could be different for different analogues and the optimal conditions are found by screening many different conditions. Crystals are obtained by the sitting drop vapor diffusion method from, for example a reservoir solution containing 0.8 M K/Na Tartrate, 0.1 M Tris pH 8.5, 0.5% PEG MME 5000. Data are collected with a rotating anode (Rigaku, MicroMax-007HF) equipped with a MarCCD detector and processed by XDS (J Appl Crystallogr 26: 795-800). The structure is solved by molecular replacement using Molrep (J Appl Crystallogr 30: 1022-1025.) with an in house structure as search model. Data refinement and model building is made using the programs Refmac (Acta Crystallogr D 53: 240-255.) and Coot (Acta Crystallogr D 60: 2126-2132.).

Example 113

Guanidinium Hydrochloride Denaturation

Guanidinium hydrochloride denaturation of selected insulin derivatives containing extra disulfide bonds can be followed by circular dichroism (CD) spectroscopy in order to determine free energy of unfolding. Upon protein denaturation, negative CD in the far UV range (240-218-nm)

gradually diminishes, consistent with the loss of ordered secondary structure that accompanies protein unfolding. The far-UV CD spectrum of human insulin is sensitive to both protein unfolding and self-association (Holladay et al., 1977 Biochim. Biophys.Acta 494, 245-254.; Melberg & Johnson, 1990, Biochim. Biophys.Acta 494, 245-254.). In order to separate these phenomena at pH 8, GuHCl titrations is carried out at different protein concentrations, e.g. 3, 37, and 250 µM. At these concentrations, insulin analogues exists mainly as monomers, dimers and mixture of dimers and higher aggregates. The insulin CD spectrum in the near UV range (330-250-nm) reflects the environment of the tyrosine chromophore with contributions from the disulfide linkages (Morris et al., 1968, Biochim. Biophys. Acta. 160, 145-155.; Wood et al., 1975, Biochim. Biophys. Acta. 160, 145-155.; Strickland & Mercola, 1976, Biochemistry 15, 3875-3884.). Plots of changes in molar elipticities at both near UV and far UV regions as a function of denaturant concentration isbe generated. Free energy of unfolding was previously calculated from such insulin denaturation curves fitted with two state model (Kaarsholm, N. C. et al 1993 Biochemistry, 32, 10773-8).

Protein concentrations is determined by UV absorbance and/or RP-HPLC and/or SEC-HPLC. Denaturation samples are prepared by combining different ratios of protein and GuHCl stock solutions with 10 mM Tris/C104- buffer, pH 8 0. Protein stock solutions are typically 1.5 mM in 10 mM Tris/C104-, pH 8.0. GuHCl stock solutions are 8.25 M (determined by refractometry) in 10 mM Tris/C104-, pH 8.0. All CD spectra are recorded at 25° C. Far-UV CD denaturation samples are scanned from 250 to 218 nm. Typical cell path length and protein concentrations are 0.2 cm and 37 pM, respectively. Near-UV CD denaturation samples are scanned from 330 to 250 nm using l-cm path length and typically 75 pM protein. All spectra are smoothed by a Fourier transform algorithm before subtraction of the appropriate solvent blanks. In the far-UV range, Ae is based on the molar concentration of peptide bond, while in the near-UV $\Delta\epsilon$ is normalized to the molar concentration of insulin monomer.

GuHCl denaturation curves are analyzed by assuming that the folding/unfolding transition is two-state, in which case equilibrium constants can be obtained at each denaturant concentration using $K=(\Delta\epsilon_N-\Delta\epsilon)/(\Delta\epsilon-\Delta\epsilon_U)$, where $\Delta\epsilon$ is the observed value of the CD and $\Delta\epsilon_N$ and $\Delta\epsilon_U$ represent the CD values for native and unfolded forms, respectively, at the given GuHCl concentration (Pace, C. N. (1975) CRC Crit. Rev. Biochem. 3, 1-43.). Values for $\Delta\epsilon_N$ and $\Delta\epsilon_U$ at GuHCl concentrations in the transition region were obtained by linear extrapolation of the pre- and posttransition base lines into the transition region, ie., $\Delta\epsilon_N=\Delta\epsilon°_N+m_N[\text{GuHCl}]$ and $\Delta\epsilon_U=\Delta\epsilon_U+m_U$ [GuHCl], where $\Delta\epsilon°_N$ and $\Delta\epsilon°_U$ are intercepts and $m_N$ and $m_U$ are slopes of the pre- and posttransition base lines, respectively. The free energy of unfolding at a given denaturant concentration in the transition zone is given by $\Delta G=-RT \ln K$. We assume a linear dependence of $\Delta G$ on denaturant concentration: $\Delta G=\Delta G_{H2O}-m[\text{GuHCl}]$, where $\Delta G_{H2O}$ is the value of $\Delta G$ in the absence of denaturant and m is a measure of the dependence of $\Delta G$ on denaturant concentration. Hence, $\Delta G$ values derived from K in the transition zone may be extrapolated back to 0 M denaturant to give $\Delta G_{H2O}$. The relationship between $\Delta\epsilon$ and [GuHCl] for the complete unfolding curve is shown in eq 1 (Santoro, M. M., & Bolen, D. W. (1988) Biochemistry 27, 8063-8068.):

$$\Delta\epsilon=\{(\Delta\epsilon°_N+m_N[\text{GuHCl}])+(\Delta\epsilon°_U+m_U[\text{GuHCl}])\exp[-(\Delta G_{H2O}-m[GuHCl])/RT]\}/\{(l+\exp[-(\Delta G_{H2O}-m[\text{GuHCl}])/RT]\}$$

With $\Delta\epsilon$ as the response and [GuHCl] as the independent variable, this equation is subjected to nonlinear least-squares analysis using, for example the NLIN procedure of PC SAS (SAS Inc., Cary, N.C.). Six parameters then describe the denaturation curve: $\Delta\epsilon°_N$, $\Delta\epsilon°_U$, $m_N$, $m_U$, m, and $\Delta G_{H2O}$. In addition, the GuHCl concentration at the midpoint of the denaturation curve, $C_{mid}$, is given by $\Delta G_{H2O}/m$. The difference in the free energy of unfolding between human and mutant insulins may then be calculated from $\Delta\Delta G_{H2O}=\Delta G_{H2O}(\text{mutant})-\Delta G_{H2O}(\text{wild type})$.

Example 114

Accurate Intact Mass Determination

LC-MS instrumentation consists of Acquity UPLC system (Waters, Milford, Mass.) and Synapt G2 mass spectrometer (Waters, Milford, Mass.). Insulin analogues are applied to a C18 reversed-phase HPLC column and analyzed using a linear gradient of acetonitrile in 0.05% trifluoroacetic acid. The flow from HPLC is applied directly to the electrospray interface of the Synapt G2 operating in the positive MS only mode with 2500 V capillary potential, 110° C. source temperature, 250° C. desolvation temperature and cone gass flow ($N_2$) of 50 L/h. MS spectra from m/z=100 to m/z=3000 are acquired twice per second. Instrument is calibrated by a standard mixture of NaI prior to analyses and lock spray of leucine enkephalin is applied during LC-MS analyses. Intact insulin masses are reconstructed by BioPharmaLynx 1.2 (Waters, Milford, Mass.) using MaxEnt3 algorithm. Orbitrap XL mass spectrometer (Thermo Fisher) can be used instead of Synapt G2. Orbitrap instrument is operated in the positive MS mode with source voltage of 4 kV, source current of 100 pA, sheath gass flow of 40, auxilliary gas flow of 10, sweep gas flow of 5, capillary voltage of 20 V. All MS parameters are adjusted during tuning of the instruments for optimal performance and may deviate slightly from those given above. Mass accuracy obtained by this method is better than 10 ppm.

Column: Acquity BEH C18 1×150 mm, 1.7 µm (Waters)
Flow: 0.1 ml/min
Buffer A: 0.02% (v/v) or 0.05% (v/v) TFA
Buffer B: 0.02% (v/v) or 0.04% (v/v) TFA in acetonitrile
Gradient: 5% B for 2 min; 5% B to 50% B in 12 min, 50% B to 90% B in 1 min
UV Detection: 215 nm

The invention claimed is:

1. An insulin derivative selected from the group consisting of A10C, A14E, B4C, B25H, B29K(N$^e$Octadecanedioyl-gGlu-OEG-OEG), desB30 human insulin, A10C, A14E, B3C, B25H, B29K(N(eps)Octadecanedioyl-gGlu), desB30 human insulin, A10C, A14E, B3C, B25H, B29K(N$^e$Octadecanedioyl), desB30 human insulin, A10C, A14E, B3C, B25H, B29K(N$^e$Octadecanedioyl-gGlu), desB30 human insulin, A10C, A14E, desB1, B4C, B25H, B29K(N$^e$Octadecanedioyl-gGlu-2xOEG), desB30 human insulin, A10C, A14H, B4C, B25H, B29K(N$^e$Octadecanedioyl-gGlu-2xOEG), desB30 human insulin, A10C, A14E, B3C, B25H, B29K(N$^e$Eicosanedioyl-gGlu-2xOEG), desB30 human insulin, A10C, A14E, B1C, B25H, B29K(N$^e$Eicosanedioyl-gGlu-2xOEG), desB30 human insulin, A10C, A14E, B4C, B25H, B29K(N$^e$Octadecanedioyl-gGlu), desB30 human insulin, A10C, A14E, B3C, B25H, B29K(N$^e$Octadecanedioyl-gGlu-OEG-OEG), desB30 human insulin, A10C, A14E, B3C, B25H, B29K(N$^e$Octadecanedioyl-gGlu-gGlu), desB30 human insulin, A10C, A14E, B4C, B25H, desB27, B29K(N$^e$Octadecanedioyl-gGlu), desB30 human insulin, A10C, A14E, B4C, B25H, B29K(N$^e$Octadecanedioyl), desB30 human insulin, A10C, A14E, B4C, B25H, B29K (N$^e$Octadecanedioyl-gGlu-gGlu), desB30 human insulin, A10C, A14E, B2C, B25H, B29K(N$^e$Octadecanedioyl-gGlu-OEG-OEG), desB30 human insulin, A10C, A14E, B1C, B25H, B29K(N$^e$Octadecanedioyl-gGlu-OEG-OEG), desB30 human insulin, A10C, A14E, B3C, B16H, B25H, B29K(N$^e$Eicosanedioyl-gGlu-OEG-OEG), desB30 human insulin, A10C, A14E, B4C, B25H, B29K(N$^e$Myristyl), desB30 human insulin, A10C, B4C, B29K(N$^e$Myristyl), desB30 human insulin, A10C, A14E, B3C, B25H, desB27, B29K(N(eps)octadecanedioyl-gGlu), desB30 human insulin, A10C, A14E, B3C, B25H, desB27, B29K(N(eps)octadecanedioyl-gGlu-2xOEG), desB30 human insulin, A10C, A14E, B3C, B25H, B29K(N$^e$Eicosanedioyl-gGlu), desB30 human insulin, A10C, A14E, B4C, B25H, B29K(N(eps) eicosanedioyl-gGlu-2xOEG), desB30 human insulin, A10C, A14E, B3C, B25H, desB27, B29K(N(eps)eicosanedioyl-gGlu), desB30 human insulin, A10C, A14E, B3C, B25H, desB27, B29K(N(eps)eicosanedioyl-gGlu-2xOEG), desB30 human insulin, A10C, A14E, B4C, B25H, B29K(N$^e$Hexadecanedioyl-gGlu), desB30 human insulin, A10C, A14E, B4C, B25H, B29K(N$^e$Hexadecanedioyl-gGlu-OEG-OEG), desB30 human insulin, A10C, A14E, B4C, B25H, B29K (N$^e$Hexadecanedioyl), desB30 human insulin, A10C, A14E, B4C, B25H, B29K(N$^e$Hexadecanedioyl-gGlu-gGlu), desB30 human insulin, A10C, A14E, B4C, B25H, desB27, B29K(N$^e$Octadecanedioyl-gGlu-OEG-OEG), desB30 human insulin, A10C, A14E, B4C, B25H, desB27, B29K (N$^e$Octadecanedioyl-gGlu-gGlu), desB30 human insulin, A10C, A14E, B4C, B25H, desB27, B29K(N$^e$Hexadecanedioyl-gGlu-OEG-OEG), desB30 human insulin, A10C, A14E, B4C, B25H, desB27, B29K(N$^e$Hexadecanedioyl-gGlu), desB30 human insulin, A10C, A14E, B3C, B25H, B29K(N$^e$Hexadecanedioyl-gGlu), desB30 human insulin, A10C, A14E, B3C, B25H, B29K(N$^e$Hexadecanedioyl-gGlu-OEG-OEG), desB30 human insulin, A10C, A14E, B2C, B25H, B29K(N$^e$Hexadecanedioyl-gGlu-OEG-OEG), desB30 human insulin, A10C, A14E, B2C, B25H, B29K (N$^e$Hexadecanedioyl-gGlu), desB30 human insulin, A10C, A14E, B2C, B25H, B29K(N$^e$Octadecanedioyl-gGlu), desB30 human insulin, A10C, A14E, B1C, B25H, B29K (N$^e$Octadecanedioyl-gGlu), desB30 human insulin, A10C, A14E, B1C, B25H, B29K(N$^e$Hexadecanedioyl-gGlu-OEG-OEG), desB30 human insulin, A10C, A14E, B1C, B25H, B29K(N$^e$Hexadecanedioyl-gGlu), desB30 human insulin, A10C, B1C, B29K(N$^e$Hexadecanedioyl-gGlu-OEG-OEG), desB30 human insulin A10C, B1C, B29K(N$^e$Hexadecanedioyl-gGlu), desB30 human insulin, A10C, B1C, B29K (N$^e$Octadecanedioyl-gGlu-OEG-OEG), desB30 human insulin, A10C, B1C, B29K(N$^e$Octadecanedioyl-gGlu), desB30 human insulin, A10C, B2C, B29K(N$^e$Octadecanedioyl-gGlu-OEG-OEG), desB30 human insulin, A10C, B2C, B29K(N$^e$Octadecanedioyl-gGlu), desB30 human insulin, A10C, B2C, B29K(N$^e$Hexadecanedioyl-gGlu-OEG-OEG), desB30 human insulin, A10C, B2C, B29K (N$^e$Hexadecanedioyl-gGlu), desB30 human insulin, A10C, B3C, B29K(N$^e$Hexadecanedioyl-gGlu), desB30 human insulin, A10C, B3C, B29K(N$^e$Hexadecanedioyl-gGlu-OEG-OEG), desB30 human insulin, A10C, B3C, B29K (N$^e$Octadecanedioyl-gGlu-OEG-OEG), desB30 human insulin, A10C, B3C, B29K(N$^e$Octadecanedioyl-gGlu), desB30 human insulin, A10C, B4C, B29K(N$^e$Octadecanedioyl-gGlu), desB30 human insulin, A10C, B4C, B29K (N$^e$Octadecanedioyl-gGlu-OEG-OEG), desB30 human insulin, A10C, B4C, B29K(N$^e$Hexadecanedioyl-gGlu-OEG-OEG), desB30 human insulin, A10C, B4C, B29K (N$^e$Hexadecanedioyl-gGlu), desB30 human insulin, A10C, A14E, B1C, B16H, B25H, B29K(N$^e$eicosanedioyl-gGlu-2xOEG), desB30 human insulin, A10C, A14E, B1C, B16H, B25H, B29K(N$^e$eicosanedioyl-gGlu), desB30 human insulin, A10C, A14E, B1C, B16H, B25H, B29K(N$^e$Octadecanedioyl-gGlu-OEG-OEG), desB30 human insulin, A10C, A14E, B1C, B16H, B25H, B29K(N$^e$Octadecanedioyl-gGlu), desB30 human insulin, A10C, A14E, B1C, B16H, B25H, B29K(N$^e$Hexadecanedioyl-gGlu), desB30 human insulin, A10C, A14E, B1C, B16H, B25H, B29K(N$^e$Hexadecanedioyl-gGlu-OEG-OEG), desB30 human insulin, A10C, A14E, B2C, B16H, B25H, B29K(N$^e$Hexadecanedioyl-gGlu-OEG-OEG), desB30 human insulin, A10C,
A14E, B2C, B16H, B25H, B29K(N$^e$Hexadecanedioyl-gGlu), desB30 human insulin, A10C, A14E, B2C, B16H, B25H, B29K(N$^e$Octadecanedioyl-gGlu), desB30 human insulin, A10C, A14E, B2C, B16H, B25H, B29K(N$^e$Octadecanedioyl-gGlu-OEG-OEG), desB30 human insulin, A10C, A14E, B2C, B16H, B25H, B29K(N$^e$Eicosanedioyl-gGlu-OEG-OEG), desB30 human insulin, A10C, A14E, B2C, B16H, B25H, B29K(N$^e$Eicosanedioyl-gGlu), desB30 human insulin, A10C, A14E, B3C, B16H, B25H, B29K (N$^e$Eicosanedioyl-gGlu), desB30 human insulin, A10C, A14E, B3C, B16H, B25H, B29K(N$^e$Octadecanedioyl-gGlu-OEG-OEG), desB30 human insulin, A10C, A14E, B3C, B16H, B25H, B29K(N$^e$Octadecanedioyl-gGlu), desB30 human insulin, A10C, A14E, B3C, B16H, B25H, B29K (N$^e$Hexadecanedioyl-gGlu), desB30 human insulin, A10C, A14E, B3C, B16H, B25H, B29K(N$^e$Hexadecanedioyl-gGlu-OEG-OEG), desB30 human insulin, A10C, A14E, B4C, B16H, B25H, B29K(N$^e$Hexadecanedioyl-gGlu-OEG-OEG), desB30 human insulin, A10C, A14E, B4C, B16H, B25H, B29K(N$^e$Hexadecanedioyl-gGlu), desB30 human insulin, A10C, A14E, B4C, B16H, B25H, B29K(N$^e$Octadecanedioyl-gGlu), desB30 human insulin, A10C, A14E, B4C, B16H, B25H, B29K(N$^e$Octadecanedioyl-gGlu-OEG-OEG), desB30 human insulin, A10C, A14E, B4C, B16H, B25H, B29K(N$^e$Eicosanedioyl-gGlu-OEG-OEG), desB30 human insulin, A10C, A14E, B4C, B16H, B25H, B29K(N$^e$Eicosanedioyl-gGlu), desB30 human insulin, A10C, A14E, B1C, B25H, B29K(N(eps)eicosanedioyl-gGlu), desB30 human insulin, A10C, A14E, B2C, B25H, B29K(N(eps) eicosanedioyl-gGlu), desB30 human insulin, A10C, A14E, B2C, B25H, B29K(N(eps)eicosanedioyl-gGlu-2xOEG), desB30 human insulin, A10C, A14E, B4C, B25H, desB27, B29K(N(eps)eicosanedioyl-gGlu), desB30 human insulin, A10C, A14E, B4C, B25H, desB27, B29K(N(eps)eicosanedioyl-gGlu-2xOEG), desB30 human insulin, A10C, A14E, B4C, B25H, B29K(N(eps)eicosanedioyl-gGlu), desB30 human insulin, A10C, A14E, B3C, B25H, desB27, B29K (N(eps)hexadecanedioyl-gGlu), desB30 human insulin, A10C, A14E, B3C, B25H, desB27, B29K(N(eps)hexadecanedioyl-gGlu-2xOEG), desB30 human insulin, A10C, A14E, B3C, desB27, B29K(N(eps)hexadecanedioyl-gGlu), desB30 human insulin, A10C, A14E, B3C, desB27, B29K (N(eps)hexadecanedioyl-gGlu-2xOEG), desB30 human insulin, A10C, A14E, B3C, desB27, B29K(N(eps)octadecanedioyl-gGlu), desB30 human insulin, A10C, A14E, B3C, desB27, B29K(N(eps)octadecanedioyl-gGlu-2xOEG), desB30 human insulin, A10C, A14E, B3C, desB27, B29K (N(eps)eicosanedioyl-gGlu), desB30 human insulin, A10C, A14E, B3C, desB27, B29K(N(eps)eicosanedioyl-gGlu-2xOEG), desB30 human insulin, A10C, A14E, B3C, B16H, B25H, B29K(N(eps)eicosanedioyl-2xgGlu), desB30 human insulin, A10C, A14E, B3C, B16E, B25H, B29K(N(eps) eicosanedioyl-gGlu-2xOEG), desB30 human insulin, A10C, A14E, B4C, B16E, B25H, B29K(N(eps)eicosanedioyl-gGlu-2xOEG), desB30 human insulin, A10C, A14E, B3C, B16H, B25H, B29K(N(eps)eicosanedioyl-2xgGlu), desB30 human insulin, and A10C, A14E, B4C, B16E, B25H, B29K (N(eps)eicosanedioyl-2xgGlu), desB30 human insulin.

2. A pharmaceutical composition comprising a biologically active amount of an insulin derivative according to claim 1 and a pharmaceutically acceptable carrier.

3. A method for the treatment of diabetes mellitus in a subject in need thereof comprising administering to said subject the pharmaceutical composition according to claim 2.

4. A method for the treatment of diabetes mellitus in a subject in need thereof comprising administering to said subject an insulin derivative according to claim 1.

5. A process for preparing a pharmaceutical composition comprising mixing an insulin derivative according to claim 1 with a pharmaceutically acceptable excipient.

* * * * *